US008735345B2

(12) United States Patent
Porter et al.

(10) Patent No.: US 8,735,345 B2
(45) Date of Patent: May 27, 2014

(54) THERAPEUTIC COMPOSITION

(75) Inventors: Steven B. Porter, Mill Valley, CA (US); Williamson Ziegler Bradford, Ross, CA (US); Patrick F. Smith, Pleasanton, CA (US); Ellen S. Yetzer, San Francisco, CA (US); Abel De La Rosa, Alpharetta, GA (US); Michael D. Rogers, Chapel Hill, NC (US); William T. Symonds, Cary, NC (US)

(73) Assignees: Hoffmann la Roche Inc., Nutley, NJ (US); Pharmasset, Inc., Princeton, NJ (US); Roche Palo Alto LLC, Palo Alto, CA (US)

( * ) Notice: Subject to any disclaimer, the term of this patent is extended or adjusted under 35 U.S.C. 154(b) by 614 days.

(21) Appl. No.: 12/713,497

(22) Filed: Feb. 26, 2010

(65) Prior Publication Data

US 2010/0221217 A1 Sep. 2, 2010

Related U.S. Application Data

(60) Provisional application No. 61/156,414, filed on Feb. 27, 2009, provisional application No. 61/257,367, filed on Nov. 2, 2009.

(51) Int. Cl.
*A61K 38/06* (2006.01)
*A61K 38/12* (2006.01)

(52) U.S. Cl.
USPC .......................................................... 514/4.3

(58) Field of Classification Search
None
See application file for complete search history.

(56) References Cited

U.S. PATENT DOCUMENTS

| | | | |
|---|---|---|---|
| 5,034,394 A | 7/1991 | Daluge | |
| 5,149,820 A | 9/1992 | Borretzen et al. | |
| 5,232,928 A | 8/1993 | Skiles | |
| 5,624,949 A | 4/1997 | Heath et al. | |
| 5,656,627 A | 8/1997 | Bemis et al. | |
| 5,756,466 A | 5/1998 | Bemis et al. | |
| 5,847,135 A | 12/1998 | Bemis et al. | |
| 5,968,895 A | 10/1999 | Gefter et al. | |
| 6,329,417 B1 | 12/2001 | Llinas-Brunet et al. | |
| 6,376,531 B1 | 4/2002 | Bell | |
| 6,608,027 B1 | 8/2003 | Tsantrizos et al. | |
| 6,642,204 B2 | 11/2003 | Llinas-Brunet et al. | |
| 6,693,072 B2 | 2/2004 | Gallion et al. | |
| 6,767,991 B1 | 7/2004 | Llinas-Brunet et al. | |
| 6,818,200 B2 | 11/2004 | Foster et al. | |
| 6,846,802 B2 | 1/2005 | Chen et al. | |
| 6,858,600 B2 | 2/2005 | Hamilton et al. | |
| 6,867,303 B2 | 3/2005 | Grela | |
| 6,909,000 B2 | 6/2005 | Farmer et al. | |
| 6,919,423 B2 | 7/2005 | Llinas-Brunet | |
| 7,012,066 B2 | 3/2006 | Saksena et al. | |
| 7,132,504 B2 | 11/2006 | Scola et al. | |
| 7,208,600 B2 | 4/2007 | Cottrell et al. | |
| 7,273,885 B2 | 9/2007 | Pitlik et al. | |
| 7,491,794 B2 | 2/2009 | Blatt et al. | |
| 7,829,665 B2 | 11/2010 | Blatt et al. | |
| 2002/0016294 A1 | 2/2002 | Venkatraman et al. | |
| 2002/0016442 A1 | 2/2002 | Llinas-Brunet et al. | |
| 2002/0037998 A1 | 3/2002 | Llinas-Brunet et al. | |
| 2002/0107181 A1 | 8/2002 | Chen et al. | |
| 2002/0111313 A1 | 8/2002 | Campbell et al. | |
| 2003/0181363 A1 | 9/2003 | Llinas-Brunet et al. | |
| 2003/0186895 A1 | 10/2003 | Llinas-Brunet et al. | |
| 2003/0191067 A1 | 10/2003 | Llinas-Brunet et al. | |
| 2003/0195228 A1 | 10/2003 | Chen et al. | |
| 2003/0224977 A1 | 12/2003 | Llinas-Brunet et al. | |
| 2003/0236242 A1 | 12/2003 | Perni et al. | |
| 2004/0002448 A1 | 1/2004 | Tsantrizos et al. | |
| 2004/0018986 A1 | 1/2004 | Pitlik et al. | |
| 2004/0038872 A1 | 2/2004 | Campbell et al. | |
| 2004/0048802 A1 | 3/2004 | Ripka et al. | |
| 2004/0072761 A1 | 4/2004 | Campbell et al. | |
| 2004/0077551 A1 | 4/2004 | Campbell et al. | |
| 2004/0106559 A1 | 6/2004 | Wang et al. | |
| 2004/0138109 A1 | 7/2004 | Chen et al. | |
| 2004/0180815 A1 | 9/2004 | Nakajima et al. | |
| 2004/0229776 A1 | 11/2004 | Chen et al. | |
| 2004/0229777 A1 | 11/2004 | Cerreta et al. | |
| 2004/0229848 A1 | 11/2004 | Demuth et al. | |
| 2004/0242887 A1 | 12/2004 | Alken et al. | |
| 2004/0259804 A1 | 12/2004 | Karanewsky et al. | |
| 2005/0009737 A1 | 1/2005 | Clark | |

(Continued)

FOREIGN PATENT DOCUMENTS

| | | |
|---|---|---|
| CA | 2370400 | 8/2003 |
| CL | 39715 | 3/1996 |
| CL | 01958-96 | 7/1997 |
| CL | 2703-97 | 12/1997 |
| CL | 39715 | 6/1998 |
| CL | 2703-97 | 8/1998 |
| CL | 01184-98 | 3/1999 |
| CL | 1797-99 | 8/1999 |
| CL | 1804-99 | 8/1999 |
| CL | 795-00 | 4/2000 |
| CL | 795-00 | 3/2001 |

(Continued)

OTHER PUBLICATIONS

Jantzen. Modern Pharmaceutics, 1996, 596.*

(Continued)

*Primary Examiner* — Noble Jarrell
(74) *Attorney, Agent, or Firm* — Bryan Cave LLP

(57) ABSTRACT

Embodiments disclosed in the present application relate to a composition that can include a hepatitis C viral polymerase inhibitor, or pharmaceutically acceptable salt or prodrug thereof and a hepatitis C viral protease inhibitor, or pharmaceutically acceptable salt or prodrug thereof. Additional embodiments disclosed relate to methods for treating a disease condition such as a hepatitis C virus infection, liver fibrosis and/or impaired liver function with a hepatitis C viral polymerase inhibitor, or pharmaceutically acceptable salt or prodrug thereof and a hepatitis C viral protease inhibitor, or pharmaceutically acceptable salt or prodrug thereof.

70 Claims, 4 Drawing Sheets

(56) References Cited

U.S. PATENT DOCUMENTS

| | | |
|---|---|---|
| 2005/0049187 A1 | 3/2005 | Brandenburg et al. |
| 2005/0065073 A1 | 3/2005 | Wu et al. |
| 2005/0080017 A1 | 4/2005 | Cottrell et al. |
| 2005/0090432 A1 | 4/2005 | McPhee et al. |
| 2005/0119189 A1 | 6/2005 | Cottrell et al. |
| 2005/0119453 A1 | 6/2005 | Brenner et al. |
| 2005/0136400 A1 | 6/2005 | Lin et al. |
| 2005/0143316 A1 | 6/2005 | Tu et al. |
| 2005/0153877 A1 | 7/2005 | Miao et al. |
| 2005/0153900 A1 | 7/2005 | Velazquez et al. |
| 2005/0192212 A1 | 9/2005 | Llinas-Brunet et al. |
| 2005/0197301 A1 | 9/2005 | Njoroge et al. |
| 2005/0209135 A1 | 9/2005 | Busacca et al. |
| 2005/0215486 A1 | 9/2005 | Cottrell et al. |
| 2005/0215513 A1 | 9/2005 | Boojamra et al. |
| 2005/0215525 A1 | 9/2005 | Boojamra et al. |
| 2005/0222047 A1 | 10/2005 | Chen et al. |
| 2005/0222238 A1 | 10/2005 | Alken et al. |
| 2005/0245458 A1 | 11/2005 | Arasappan et al. |
| 2005/0261200 A1 | 11/2005 | Miao et al. |
| 2005/0267018 A1 | 12/2005 | Blatt et al. |
| 2005/0267043 A1 | 12/2005 | Bogen et al. |
| 2005/0267151 A1 | 12/2005 | Busacca et al. |
| 2005/0272663 A1 | 12/2005 | Arasappan et al. |
| 2006/0009667 A1 | 1/2006 | Herweck et al. |
| 2006/0019905 A1 | 1/2006 | Bailey et al. |
| 2006/0046956 A1 | 3/2006 | Sannigrahi et al. |
| 2006/0063915 A1 | 3/2006 | Gallou et al. |
| 2006/0069099 A1 | 3/2006 | Fu et al. |
| 2006/0122123 A1 | 6/2006 | Chaudhary et al. |
| 2006/0128692 A1 | 6/2006 | Chen et al. |
| 2006/0183694 A1 | 8/2006 | Sin et al. |
| 2006/0198824 A1 | 9/2006 | Malcolm et al. |
| 2006/0205638 A1 | 9/2006 | Busacca et al. |
| 2006/0210969 A1 | 9/2006 | Rice et al. |
| 2006/0269516 A1 | 11/2006 | Presta et al. |
| 2006/0275366 A1 | 12/2006 | Malcolm et al. |
| 2006/0276405 A1 | 12/2006 | Albrecht |
| 2007/0010455 A1 | 1/2007 | Hewawasam et al. |
| 2007/0027071 A1 | 2/2007 | Holloway et al. |
| 2007/0032433 A1 | 2/2007 | Saksena et al. |
| 2007/0054842 A1 | 3/2007 | Blatt et al. |
| 2007/0054864 A1 | 3/2007 | Graupe et al. |
| 2007/0072809 A1 | 3/2007 | Cho et al. |
| 2007/0093414 A1 | 4/2007 | Carini et al. |
| 2007/0099825 A1 | 5/2007 | D'Andrea et al. |
| 2007/0112001 A1 | 5/2007 | Anselm et al. |
| 2007/0161574 A1 | 7/2007 | Rosenquist et al. |
| 2007/0197448 A1 | 8/2007 | Velazquez et al. |
| 2007/0231262 A1 | 10/2007 | Lin et al. |
| 2007/0281885 A1 | 12/2007 | Sun et al. |
| 2007/0299078 A1 | 12/2007 | Niu et al. |
| 2008/0014173 A1 | 1/2008 | Scola et al. |
| 2008/0019942 A1 | 1/2008 | Seiwert et al. |
| 2008/0032936 A1 | 2/2008 | Gai et al. |
| 2008/0038225 A1 | 2/2008 | Sun et al. |
| 2008/0039470 A1 | 2/2008 | Niu et al. |
| 2008/0107623 A1 | 5/2008 | D'Andrea et al. |
| 2008/0107624 A1 | 5/2008 | D'Andrea et al. |
| 2008/0107625 A1 | 5/2008 | D'Andrea et al. |
| 2008/0119461 A1 | 5/2008 | Sin et al. |
| 2008/0125444 A1 | 5/2008 | Sun et al. |
| 2008/0267916 A1 | 10/2008 | Gai et al. |
| 2008/0267917 A1 | 10/2008 | Niu et al. |
| 2008/0267918 A1 | 10/2008 | Gai et al. |
| 2008/0269228 A1 | 10/2008 | Moore et al. |
| 2008/0269502 A1 | 10/2008 | Gantz et al. |
| 2008/0274080 A1 | 11/2008 | Or et al. |
| 2008/0274082 A1 | 11/2008 | Gai et al. |
| 2008/0279821 A1 | 11/2008 | Niu et al. |
| 2008/0286230 A1 | 11/2008 | Sommadossi et al. |
| 2008/0317712 A1 | 12/2008 | Niu et al. |
| 2009/0005387 A1 | 1/2009 | Niu et al. |
| 2009/0035267 A1 | 2/2009 | Moore et al. |
| 2009/0035268 A1 | 2/2009 | Sun et al. |
| 2009/0035272 A1 | 2/2009 | Moore et al. |
| 2009/0041721 A1 | 2/2009 | Niu et al. |
| 2009/0047244 A1 | 2/2009 | Parsy et al. |
| 2009/0047248 A1 | 2/2009 | Sun et al. |
| 2009/0048297 A1 | 2/2009 | Phadke et al. |
| 2009/0053175 A1 | 2/2009 | Or et al. |
| 2009/0060874 A1 | 3/2009 | Qiu et al. |
| 2009/0062311 A1 | 3/2009 | Simmen et al. |
| 2009/0075869 A1 | 3/2009 | Holloway et al. |
| 2009/0082261 A1 | 3/2009 | Chen et al. |
| 2009/0082366 A1 | 3/2009 | Czarnik |
| 2009/0093533 A1 | 4/2009 | Beigelman et al. |
| 2009/0098085 A1 | 4/2009 | Sun et al. |
| 2009/0105471 A1 | 4/2009 | Blatt et al. |
| 2009/0111757 A1 | 4/2009 | Lin et al. |
| 2009/0111969 A1 | 4/2009 | Blatt et al. |
| 2009/0111982 A1 | 4/2009 | Blatt et al. |
| 2009/0123423 A1 | 5/2009 | Gai et al. |
| 2009/0123425 A1 | 5/2009 | Moore et al. |
| 2009/0130059 A1 | 5/2009 | Sun et al. |
| 2009/0148407 A1 | 6/2009 | Blatt et al. |
| 2009/0149491 A1 | 6/2009 | Liu et al. |
| 2009/0155209 A1 | 6/2009 | Blatt et al. |
| 2009/0155210 A1 | 6/2009 | Gai et al. |
| 2009/0163706 A1 | 6/2009 | Hildbrand et al. |
| 2009/0169510 A1 | 7/2009 | Blatt et al. |
| 2009/0180985 A1 | 7/2009 | Liu et al. |
| 2009/0202480 A1 | 8/2009 | Parsy et al. |
| 2009/0203008 A1 | 8/2009 | Ludmerer et al. |
| 2009/0203629 A1 | 8/2009 | Holsinger |
| 2009/0269305 A1 | 10/2009 | Seiwert et al. |
| 2009/0274657 A1 | 11/2009 | Gai et al. |
| 2009/0275714 A1 | 11/2009 | Puentener et al. |
| 2009/0285773 A1 | 11/2009 | Sun et al. |
| 2009/0285774 A1 | 11/2009 | Sin et al. |
| 2009/0286814 A1 | 11/2009 | Lin et al. |
| 2009/0286843 A1 | 11/2009 | Blatt et al. |
| 2009/0297472 A1 | 12/2009 | Wang et al. |
| 2009/0297476 A1 | 12/2009 | Seiwert et al. |
| 2010/0003217 A1 | 1/2010 | Cretton-Scott et al. |
| 2010/0022578 A1 | 1/2010 | Raboisson et al. |
| 2010/0036116 A1 | 2/2010 | Scalone et al. |
| 2010/0068176 A1 | 3/2010 | Belema et al. |
| 2010/0068182 A1 | 3/2010 | Huang et al. |
| 2010/0074867 A1 | 3/2010 | Venkatraman et al. |
| 2010/0074890 A1 | 3/2010 | Hagel et al. |
| 2010/0080770 A1 | 4/2010 | Hiebert et al. |
| 2010/0080771 A1 | 4/2010 | Hiebert et al. |
| 2010/0081700 A1 | 4/2010 | Wang et al. |
| 2010/0087382 A1 | 4/2010 | Bailey et al. |
| 2010/0119479 A1 | 5/2010 | Buckman et al. |
| 2010/0124545 A1 | 5/2010 | Zhang et al. |
| 2010/0150866 A1 | 6/2010 | Wang et al. |
| 2010/0152103 A1 | 6/2010 | Phadke et al. |
| 2010/0160403 A1 | 6/2010 | Link et al. |
| 2010/0168384 A1 | 7/2010 | McDaniel et al. |
| 2010/0173939 A1 | 7/2010 | Link et al. |
| 2010/0196321 A1 | 8/2010 | Cooper et al. |
| 2010/0215616 A1 | 8/2010 | Romine et al. |
| 2010/0221217 A1 | 9/2010 | Porter et al. |
| 2010/0260709 A1 | 10/2010 | Brandl et al. |
| 2010/0260710 A1 | 10/2010 | Parsy et al. |
| 2010/0272682 A1 | 10/2010 | Tran et al. |
| 2010/0323989 A1 | 12/2010 | Delaney et al. |
| 2010/0324059 A1 | 12/2010 | Delaney et al. |
| 2010/0324060 A1 | 12/2010 | Delaney et al. |
| 2011/0129444 A1 | 6/2011 | Buckman et al. |

FOREIGN PATENT DOCUMENTS

| | | |
|---|---|---|
| CL | 766-01 | 10/2001 |
| CL | 766-01 | 4/2002 |
| CL | 144-03 | 1/2003 |
| CL | 167-03 | 1/2003 |
| CL | 168-03 | 1/2003 |
| CL | 144-03 | 1/2004 |
| CL | 167-03 | 5/2004 |
| CL | 1161-04 | 12/2004 |
| CL | 120-05 | 1/2005 |

(56) References Cited

FOREIGN PATENT DOCUMENTS

| | | |
|---|---|---|
| CL | 1161-04 | 4/2005 |
| CL | 120-05 | 1/2006 |
| EA | 2006 07738 B1 | 12/2006 |
| EP | 0206497 A2 | 12/1986 |
| EP | 0349242 A2 | 1/1990 |
| JP | 2002/542160 | 10/2000 |
| RU | 2247126 C2 | 2/2005 |
| TW | 200510445 A | 3/2005 |
| TW | 200526685 A | 8/2005 |
| TW | 200745151 A | 12/2007 |
| WO | 95/26325 | 10/1995 |
| WO | WO 97/18207 | 5/1997 |
| WO | WO 97/43310 | 11/1997 |
| WO | WO 98/17679 | 4/1998 |
| WO | WO 98/46630 | 10/1998 |
| WO | WO 98/51665 | 11/1998 |
| WO | WO 99/07733 | 2/1999 |
| WO | WO 99/07734 | 2/1999 |
| WO | WO 99/47545 | 9/1999 |
| WO | WO 00/09543 | 2/2000 |
| WO | WO 00/09558 | 2/2000 |
| WO | WO 00/23421 | 4/2000 |
| WO | WO 00/59929 | 10/2000 |
| WO | WO 01/74768 | 10/2001 |
| WO | WO 01/81325 | 11/2001 |
| WO | WO 02/18369 | 3/2002 |
| WO | WO 02/060926 | 8/2002 |
| WO | WO 03/002518 | 1/2003 |
| WO | WO 03/053349 | 7/2003 |
| WO | WO 03/062228 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 2004/009121 | 1/2004 |
| WO | WO 2004/026896 | 4/2004 |
| WO | WO 2004/037855 | 5/2004 |
| WO | WO 2004/039833 | 5/2004 |
| WO | WO 2004/072243 | 8/2004 |
| WO | WO 2004/089974 | 10/2004 |
| WO | WO 2004/092162 | 10/2004 |
| WO | WO 2004/092203 | 10/2004 |
| WO | WO 2004/093798 | 11/2004 |
| WO | WO 2004/093915 | 11/2004 |
| WO | WO 2004/094452 | 11/2004 |
| WO | WO 2004/096286 | 11/2004 |
| WO | WO 2004/103996 | 12/2004 |
| WO | WO 2004/113365 | 12/2004 |
| WO | WO 2005/003147 | 1/2005 |
| WO | WO 2005/010029 | 2/2005 |
| WO | WO 2005/021584 | 3/2005 |
| WO | WO 2005/028501 | 3/2005 |
| WO | 2005037214 | 4/2005 |
| WO | WO 2005/035525 | 4/2005 |
| WO | WO 2005/037214 | 4/2005 |
| WO | WO 2005037214 A2 | 4/2005 |
| WO | WO 2005/039552 | 5/2005 |
| WO | WO 2005/046712 | 5/2005 |
| WO | WO 2005/051410 | 6/2005 |
| WO | WO 2005/051980 | 6/2005 |
| WO | WO 2005/056182 | 6/2005 |
| WO | WO 2005/070955 | 8/2005 |
| WO | WO 2005/073195 | 8/2005 |
| WO | WO 2005/073216 | 8/2005 |
| WO | WO 2005/075502 | 8/2005 |
| WO | WO 2005/095403 | 10/2005 |
| WO | WO 2005/097820 | 10/2005 |
| WO | WO 2005/107745 | 11/2005 |
| WO | WO 2005/113581 | 12/2005 |
| WO | WO 2006/000085 | 1/2006 |
| WO | WO 2006/020276 | 2/2006 |
| WO | WO 2006/043145 | 4/2006 |
| WO | WO 2006/045096 | 4/2006 |
| WO | WO 2006/075021 | 7/2006 |
| WO | WO 2006/113942 | 10/2006 |
| WO | WO 2006/119061 | 11/2006 |
| WO | WO 2006/122188 | 11/2006 |
| WO | WO 2007/011658 | 1/2007 |
| WO | WO 2007/011777 | 1/2007 |
| WO | WO 2007/014919 | 2/2007 |
| WO | WO 2007/014922 | 2/2007 |
| WO | WO 2007/014926 | 2/2007 |
| WO | WO 2007/014927 | 2/2007 |
| WO | WO 2007/015824 | 2/2007 |
| WO | WO 2007/016441 | 2/2007 |
| WO | WO 2007/016476 | 2/2007 |
| WO | WO 2007/017144 | 2/2007 |
| WO | WO 2007/022459 | 2/2007 |
| WO | WO 2007/030656 | 3/2007 |
| WO | WO 2007/044893 | 4/2007 |
| WO | WO 2007/044933 | 4/2007 |
| WO | WO 2007/056120 | 5/2007 |
| WO | WO 2007065829 A1 | 6/2007 |
| WO | WO 2007/089618 | 8/2007 |
| WO | WO 2007/092616 | 8/2007 |
| WO | WO 2007/104162 | 9/2007 |
| WO | WO 2007/106317 | 9/2007 |
| WO | WO 2007/111866 | 10/2007 |
| WO | WO 2007/130499 | 11/2007 |
| WO | WO 2007/133865 | 11/2007 |
| WO | WO 2007/143694 | 12/2007 |
| WO | WO 2007/146695 | 12/2007 |
| WO | WO 2007/148135 | 12/2007 |
| WO | WO 2008/005565 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021960 | 2/2008 |
| WO | WO 2008/022006 | 2/2008 |
| WO | WO 2008/033389 | 3/2008 |
| WO | WO 2008/033466 | 3/2008 |
| WO | WO 2008/046860 | 4/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057995 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/064218 | 5/2008 |
| WO | WO 2008/070358 | 6/2008 |
| WO | WO 2008/073282 | 6/2008 |
| WO | WO 2008/086161 | 7/2008 |
| WO | WO 2008/095058 | 8/2008 |
| WO | WO 2008/095999 | 8/2008 |
| WO | WO 2008/096001 | 8/2008 |
| WO | WO 2008/098368 | 8/2008 |
| WO | WO 2008/101665 | 8/2008 |
| WO | WO 2010/015545 | 8/2008 |
| WO | WO 2008/106058 | 9/2008 |
| WO | WO 2008/106130 | 9/2008 |
| WO | WO 2008/106139 | 9/2008 |
| WO | WO 2008/118332 | 10/2008 |
| WO | WO 2008/124384 | 10/2008 |
| WO | WO 2008/128121 | 10/2008 |
| WO | WO 2008/128921 | 10/2008 |
| WO | WO 2008005555 * 10/2008 ............. C07D 9/141 | |
| WO | WO 2008/134397 | 11/2008 |
| WO | WO 2008/134398 | 11/2008 |
| WO | WO 2008/137126 | 11/2008 |
| WO | WO 2008/137779 | 11/2008 |
| WO | WO 2008/141227 | 11/2008 |
| WO | WO 2009/003009 | 12/2008 |
| WO | WO 2009/005676 | 1/2009 |
| WO | WO 2009/005677 | 1/2009 |
| WO | WO 2009/005690 | 1/2009 |
| WO | WO 2009/008913 | 1/2009 |

(56) References Cited

FOREIGN PATENT DOCUMENTS

| | | |
|---|---|---|
| WO | WO 2009/035540 | 3/2009 |
| WO | WO 2009/046098 | 4/2009 |
| WO | WO 2009/051840 | 4/2009 |
| WO | WO 2009/053828 | 4/2009 |
| WO | WO 2009/064955 | 5/2009 |
| WO | WO 2009/064975 | 5/2009 |
| WO | WO 2009/067225 | 5/2009 |
| WO | WO 2009/070692 | 6/2009 |
| WO | WO 2009/073713 | 6/2009 |
| WO | WO 2009/073719 | 6/2009 |
| WO | WO 2009/073780 | 6/2009 |
| WO | WO 2009/076173 | 6/2009 |
| WO | WO 2009/079352 | 6/2009 |
| WO | WO 2009/079353 | 6/2009 |
| WO | WO 2009/080542 | 7/2009 |
| WO | WO 2009/082697 | 7/2009 |
| WO | WO 2009/082701 | 7/2009 |
| WO | WO 2009/085659 | 7/2009 |
| WO | WO 2009/094438 | 7/2009 |
| WO | WO 2009/094443 | 7/2009 |
| WO | WO 2009/108507 | 9/2009 |
| WO | WO 2009/112592 | 9/2009 |
| WO | WO 2009/124853 | 10/2009 |
| WO | WO 2009/129109 | 10/2009 |
| WO | WO 2009/134624 | 11/2009 |
| WO | WO 2009/137432 | 11/2009 |
| WO | WO 2009/142842 | 11/2009 |
| WO | WO 2009/143359 | 11/2009 |
| WO | WO 2009/143361 | 11/2009 |
| WO | WO 2009/146347 | 12/2009 |
| WO | WO 2009/149377 | 12/2009 |
| WO | WO 2009/152051 | 12/2009 |
| WO | WO 2010/011566 | 1/2010 |
| WO | WO 2011/002807 | 1/2010 |
| WO | WO 2010/017178 | 2/2010 |
| WO | WO 2010/017432 | 2/2010 |
| WO | WO 2010/028236 | 3/2010 |
| WO | WO 2010/030359 | 3/2010 |
| WO | WO 2010/033443 | 3/2010 |
| WO | WO 2010/033444 | 3/2010 |
| WO | WO 2010/033466 | 3/2010 |
| WO | WO 2010/034105 | 4/2010 |
| WO | WO 2010/048468 | 4/2010 |
| WO | WO 2010/059667 | 5/2010 |
| WO | WO 2010/065577 | 6/2010 |
| WO | WO 2010/068760 | 6/2010 |
| WO | WO 2010/072742 | 7/2010 |
| WO | WO 2010/085638 | 7/2010 |
| WO | WO 2010/107965 | 9/2010 |
| WO | WO 2010/115981 | 10/2010 |
| WO | WO 2010/116248 | 10/2010 |
| WO | WO 2010/118009 | 10/2010 |
| WO | WO 2010/121128 | 10/2010 |
| WO | WO 2010/132163 | 11/2010 |
| WO | WO 2010/135748 | 11/2010 |
| WO | WO 2010/138889 | 12/2010 |
| WO | WO 2010/151487 | 12/2010 |
| WO | WO 2010/151488 | 12/2010 |
| WO | WO 2011/002808 | 1/2011 |
| WO | WO 2011/005646 | 1/2011 |
| WO | WO 2011/014487 | 2/2011 |
| WO | WO 2011/017389 | 2/2011 |

OTHER PUBLICATIONS

Beers, et al. (Eds), "The Merck Manual of Diagnosis and Therapy", 18th Ed. 2006, Merck Research Laboratories, pp. 214-215.

Foster, Deuterium isotope effects in the metabolism of drugs and Xenobiotics: Implications for drug design, Advances in Drug Research, Academic Press, London, UK, (1985) 14: 2-40.

Thibeault et al., Use of the fused NS4A peptide-NS3 protease domain to study the importance of the helicase domain for protease inhibitor binding to hepatitis C virus NS3-NS4A, Biochemistry (Feb. 2009) 48(4): 744-753.

Murakami et al., "Mechanism of Activation of β D 2• Deoxy-2'-Fluoro-2•-C-Methylcytidine and Inhibition of Hepatitis C Virus NS5B RNA Polymerase," Antimicrobial Agents and Chemotherapy, vol. 51, pp. 503-509 (2007).

Opposition to EC Patent Application No. SP-11-11292, dated Apr. 18, 2012 (9 pages).

English translation of Opposition to EC Patent Application No. SP-11-11292 dated Apr. 18, 2012 (13 pages).

Falchi et al., 4-(4,6-Dimethoxy[1,3,5]triazin-2-yl)-4-methyl-morpholinium Chloride (DMTMM): A valuable Alternative to PyBOP for Solid Phase Peptide Synthesis, (Jan. 2000) 2: 275-277.

Kwong et al., Hepatitis C virus NS3/4A protease, Antiviral Res. (Jul. 1998) 40: 1-18.

Lamarre et al., An NS3 Protease Inhibitor with Antiviral Effects in Humans Infected with Hepatitis C Virus, Nature, (Nov. 2003) 426(6963): 186-189.

Pause et al., An NS3 Serine Protease Inhibitor Abrogates Replication of Subgenomic Hepatitits C Virus RNA, J Bio Chem., (Mar. 2003) 278(22): 20374-20380.

Šebestík et al., Acridin-9-yl Exchange: A Proposal for the Action of Some 9-Aminoacridine Drugs, Biopolymers (Peptide Science) (Aug. 2006) 84: 605-614.

Shibnev et al., 2-Methoxy-6,9-Dichloroacridine in Peptide Synthesis as a Fluorescent Label, Bioorganicheskaya Khimiuya (1984) 10(5): 610-617.

Non-final Office Action mailed Nov. 6, 2012 in U.S. Appl. No. 12/890,470 (Paper No. 20121024).

Porter et al., U.S. Appl. No. 13/203,334, filed Aug. 25, 2011, with a 371(c) date of Feb. 7, 2012.

Seiwert et al., U.S. Appl. No. 13/497,740, filed Mar. 22, 2012.

Anonymous, View of NCT00801255 on Feb. 17, 2009, XP002580349 ClinicalTrials, Retrieved from the Internet: URL:http://clinicaltrials.gov/archive/NCTO0801255/2009_02_17.

Beaulieu et al., Synthesis of (1R,2S)-1-Amino-2-vinylcyclopropanecarboxylic Acid Vinyl-ACCA) Derivatives: Key Intermediates for the Preparation of Inhibitors of the Hepatitis C Virus NS3 Protease., J. Org. Chem., 2005, 70: 5869-5879.

Bedossa et al.—The French Metavir Cooperative Study Group, "Intraobserver and Interobserver Variations in Liver Biopsy Interpretation in Patients with Chronic Hepatitis C" Hepatology, 1994, 20:15-20.

Belokon et al., A General Method for the Asymmetric Synthesis of anti-Diastereoisomers of b-Substituted L-2-Aminobutanoic Acids via Chiral Nickel Schiff's Base Complexes of Dehydroaminobutanoic Acid. X-Ray Crystal and Molecular Structure of the Nickel Complex of the Schiff's Base from [(Benzylprolyl)amino]benzophenone and Dehydroaminobutanoic Acid. , (1990) 8: 2301-2310., J. Chem. Soc. Perkin Trans. 1, 1990, 8: 2301-2310.

Blatt et al., ITMN-191 Concentrations Achieved in the Liver of Animals Promote HCV Replicon Clearance in Vitro and this Effect is Enhanced by PEG-IFN Alpha-2a, XP022087916, J Hepatol., Apr. 1, 2007, 46: S219, Abstract #576, 1 page.

Farina, Efficient Synthesis of BILN 2061, a Potent HCV Protease inhibitor, by a Convergent Approach Based on Ring-Closing Metathesis, ACS ProSpectives Conference Series, Process Chemistry in the Pharmaceutical Industry, Feb. 6-9, 2005, pp. 28.

Faucher et al., Synthesis of BILN 2061, an HCV NS3 Protease Inhibitor with Proven Antiviral Effect in Humans, Organic Letters (2004), 6(17): 2901-2904.

Foster, FRCP, Ph.D., Past, Present, and Future Hepatitis C, Seminars in Liver Disease, (2004) 24(Supp 2): 97-104.

Franciscus, ¿QuéHemos Aprendido sobre la Hepatitis C en la Conferencia AASLD de 2002? HCV Advocate at http://www.hcvadvocate.org/pdf/AASLD_2002_sp-3.pdf, 8 pages.

Galgoci et al., A convenient synthesis of methyl (Z)-1-carbamoyl-2-ethenylcyclopropanecarboxylate and (Z)-1-carbamoyl-2-ethenylcyclopropanecarboxylic acid, Synth. Commun., (1994) 24(17): 2477-2483.

(56) References Cited

OTHER PUBLICATIONS

Gane et al., Antiviral Activity of the HCV Nucleoside Polymerase Inhibitor R7128 in HCV Genotype 2 and 3 prior Non-Responders: Interim Results of R7128 1500mg BID with PEG-IFN and Ribavirin for 28 Days, Online Oct. 31, 2008 XP002580355, URL:http://www.pharmasset.com/download/Phase_I_Analysis_Cohort_4.pdf, 1 page.
Gane et al., Antiviral Activity of the HCV Nucleoside Polymerase Inhibitor R7128 in HCV Genotype 2 and 3 prior Non-Responders: Interim Results of R7128 1500mg BID with PEG-IFN and Ribavirin for 28 Days, XP 002580354, Hepatology, 48(4) Suppl, 1024A, LB10, Oct. 2008, AASLD, Abstract Only.
Gonzalez et al., Synthetic studies on L-Proline and (4R)-hydroxy-L-proline derivatives Synthesis (2004) 8: 1171-1182.
Goodman & Gilman Pharmacological Basis of Therapeutics, 9th Edition, vol. I, McGraw-Hill, Interamericana, Mexico (1996) p. 47, with partial translation, 2 pages.
Goudreau et al., Potent Inhibitors of the Hepatitis C Virus NS3 Protease: Design and Synthesis of Macrocyclic Substrate-Based (-Strand Mimics, J. Org. Chem. (2004) 69(19): 6185-6201.
Goudreau et al., The Therapeutic Potential of NS3 Protease Inhibitors in HCV Infection, Expert Opin. Investig. Drugs (2005) 1129-1144.
Hinrichsen et al., Short-term antiviral efficacy of BILN 2061, a hepatitis C virus serine protease inhibitor, in hepatitis C genotype 1 patients, Gastroenterology (2004), 127(5), 1347-1355.
Khan et al., "Diastereoselective Synthesis of trans-2-(1-Triphenylmethyl-1H-imidazol-4-yl)Cyclopropanecarboxylic Acids: Key Intermediates for the Preparation of Potent and Chiral Histamine H3 Receptor Agents" Bioorg. Med. Chem. Lett., 1997, 7(23):3017-3022.
Kwong et al., Recent Progress in the Development of Selected Hepatitis C Virus NS3-4A Protease and NS5B Polymerase Inhibitors, Curr Opin Pharmaco. Oct. 1, 2008, 8(5): 522-531.
Lalezari et al., Potent Antiviral Activity of the HCV Nucleoside Polymerase Inhibitor R7128 with Peg-IFN and Ribavirin: Interim Results of R7128 500MG BID for 28 Days, XP026661792, J Hepatol. 48, Jan. 1, 2008, S29, 66, Abstract only.
LaPlante et al., Dynamics and structure-based design of drugs targeting the critical serine protease of the hepatitis C virus from a peptidic substrate to BILN 2061., Current Medicinal Chemistry: Anti-Infective Agents, 2005, 4(2): 111-132 (Abstract Only).
Lin et al., Combination of a hepatitis C virus NS3-NS4A protease inhibitor and alpha interferon synergistically inhibits viral RNA replication and facilitates viral RNA clearance in replicon cells., Antimicrobal Agents & Chemo., 2004, 48(12): 4784-4792.
Llinas-Brunet et al., Structure-Activity Study on a Novel Series of Macrocyclic Inhibitors fo the Hepatitis C Virus NS3 Protease Leading to the Discovery of BILN 2061, J. Med. Chem. 2004, 47, 1605-1608.
Lu et al., Mutations conferring resistance to a potent hepatitis C virus serine protease inhibitor in vitro, Antimicrobial Agents and Chemotherapy (2004), 48(6): 2260-2266.
Ma et al., Accelerating Effect Induced by the Structure of a-Amino Acid in the Copper-Catalyzed Coupling Reaction of Aryl Halides with a-Amino Acids. Synthesis of Benzolactam-V8. , J Amer Chem Soc., 1998, 120: 12459-12467.
Marchetti et al., Synthesis of Two Novel Cyclic Biphenyl Ether Analogs of an Inhibitor of HCV NS3 Protease, Synlett. (1999), S1, 1000-1002.
McKenna et al., The scope and limitations of the Suzuki-Miyaura cross-coupling reactions of 6- and 8-substituted 1,2,3,4-tetrahydroisoquinoline-3-carboxylates, Tetrahedron Lett., 2001, 42, 5797-5800.
Ni et al., Progress and development of small molecule HCV antivirals, Curr. Opin. Drug Disc. Devel. (2004) 7(4): 446-459 (Abstract only).
Perni et al., Inhibitors of Hepatitis C Virus NS3• 4A protease 1. Non-Charged Tetrapeptide Variants, Bioorg. Med. Chem. Lett. (2003) 13(22): 4059-4063.
Perni et al., Inhibitors of hepatitis C virus NS3• 4A protease 2. Warhead SAR and optimization, Bioorg. Med. Chem. Lett., 2004, 14(6): 1441-6.
Perni et al., Inhibitors of hepatitis C virus NS3• 4A protease. Part 3. P2 proline variants, Bioorg. Med. Chem. Lett. (2004) 14(8): 1939-1942.
Raboisson et al., Discovery of Novel Potent and Selective Dipeptide Hepatitis C Virus NS3/4A Serine Protease Inhibitors, Bioorg & Med Chem Letters, 18(18): 5095-5100, Sep. 15, 2008.
Reddy et al., Antiviral Activity, Pharmacokinetics, Safety and Tolerability of R7128, a Novel Nucleoside HCV RNA Polymerase Inhibitor, Following Multiple, Ascending, Oral Doses in Patients with HCV Genotype 1 Infection who have Failed Prior Interferon Therapy, Hepatology 46(4): Suppl. S, 862A-863A, Oct. 2007, AASLD LB9, Abstract Only.
Rodriguez-Torres et al., Potent Antiviral Response to the HCV Nucleoside Polymerase Inhibitor R7128 for 28 Days with PEG-IFN and Ribavirin: Subanalysis by Race/Ethnicity, Weight and HCV Genotype, XP-002580352, Hepatology, 48(4) #1899, Suppl. 1160A, AASLD, Abstract Only, 2008.
Rodriguez-Torres et al., Potent Antiviral Response to the HCV Nucleoside Polymerase Inhibitor R7128 for 28 Days with PEG-IFN and Ribavirin: Subanalysis by Race/Ethnicity, Weight and HCV Genotype, XP002580353, Online Oct. 31, 2008, URL:http://www.pharmasset.com/download/Phase_I_Subanalysis_Cohrts_1_2_3.pdf, 1 page.
Ronn et al., Exploration of Acyl Sulfonamides as Carboxylic Acid Replacements in Protease Inhibitors of the Hepatitis C Virus Full-length NS3, Bioorg & Med Chem., 14(2): 544-559, Jan. 15, 2006.
Seiwert et al., Preclinical Characteristics of the Hepatitis C Virus NS3/4A Protease Inhibitor ITMN-191 (R7227), Antimicro Agents Chemother., Dec. 2008, 52(12): 4432-4441.
Simmen et al., "Preclinical characterization of TMC435350, a novel macrocyclic inhibitor of the HCV NS3/4A serine protease", Tibotec Poster, Mechelen, Belgium, 14th International Symposium on Hepatitis C Virus & Related Viruses, Glasgow, UK, Sep. 9, 2007, 1 page.
Sulkowski, "Orally available Hepatitis C Virus (HCV) protease inhibitor (BILN 2061) demonstrates potent anti-viral activity in persons infected with HCV genotype 1" AASLD Conference Report (2002) 1 page, Link: www.natap.org/2002/AASLD/day14.htm.
Sun et al., P4 cap modified tetrapeptidyl (-ketoamides as potent HCV NS3 protease inhibitors, Bioorg. Med. Chem. Lett. (2004) 14(16): 4333-4338.
Tan et al., Combination of the NS3/4A Protease Inhibitor ITMN-191 (R7227) with the Active Moiety of the NS5B Inhibitors R1626 or R7128 Enhances Replicon Clearance and Reduces the Emergence of Drug Resistant Variant, Oct. 31, 2008, XP002580351, URL:http://www.pharmasset.com/download/Tan_PSI7851_AASLD%20Oct08.pdf, 1 page.
Tan et al., Combination of the NS3/4A Protease Inhibitor ITMN-191 9R7227) with the Active Moiety of the NS5B Inhibitors R1626 or R7128 Enhances Replicon Clearance and Reduces the Emergence of Drug Resistant Variants, XP-002580350, Hepatology, Oct. 2008, 48(4) Suppl. 1153A, AASLD, Abstract Only.
The Merck Index, An Encyclopedia of Chemicals, Drugs, and Biologicals, "Abacavir", 14th Edition, 2006, p. 1.
The Merck Index, an Encyclopedia of Chemicals, Drugs, and Biologicals, "Didanosine", 14th Edition, 2006, p. 525.
Thibeault et al., Sensitivity of NS3 serine proteases from hepatitis C virus genotypes 2 and 3 to the inhibitor BILN 2061, J. Virol., (2004) 78(14): 7352-7359.
Thorstensson et al., Synthesis of Novel Potent Hepatitis C Virus NS3 Protease Inhibitors. Discovery of 4-Hydroxy-cyclopent-2ene-1,2-dicarboxylic Acid as a N-Acyl-L-Hydroxy-proline Bioisostere, Bioorg. Med. Chem. (2006), 16: 827-838.
Tsantrizos et al., Macrocyclic Inhibitors of the NS3 Protease as Potential Therapeutic Agents of Hepatitis C Virus Infection. , Angew. Chem. Int. Ed. (2003), 42(12):1356-1360.
Tsantrizos, The design of a potent inhibitor of the hepatitis C virus NS3 protease: BILN 2061—From the NMR tube to the clinic, Biopolymers (2004), 76(4): 309-323 (Abstract Only).
www.medknowledge.de/neu/2002/IV-2002-32-biln-2061-pipeline.htm, pp. 1-4.

(56) References Cited

OTHER PUBLICATIONS

Yao et al., "Molecular views of viral polyprotein processing revealed by the crystal structure of the hepatitis C virus bifunctional protease-helicase," Structure, 1999, 7(11):1353-1363.

Zhou et al., Phenotypic and Structural Analyses of Hepatitis C Virus NS3 Protease Arg155 Variants, Jun. 6, 2007, J Bio Chem., 282(31): 22619-22628.

Zucca et al., Regioselective Solid-phase 4-Amino-de-chlorination of 2,3,6-Trichloropyrimidine by Resin-supported N-Potassium Carbamates, Tetra Lttr., 2001, 42: 1033-1035.

International Search Report and Written Opinion dated Jun. 7, 2010 in Application No. PCT/US2010/025611, filed Feb. 26, 2010.

\* cited by examiner

β-D-2'-deoxy-2'-fluoro-2'-C-methylcytidine
(Compound 1)

Diisobutyl ester prodrug of β-D-2'-deoxy-2'-fluoro-2'-C-methylcytidine
(Compound 1a)

(1S, 4R, 6S, 14S, 18R)-4-Fluoro-1,3-dihydro-isoindole-2-carboxylic acid 14-tertbutoxycarbonylamino-4-cyclopropanesulfonylaminocarbonyl-2,15-dioxo-3,16-diaza-tricyclo[14.3.0.04,6]nonadec-7-en-18-yl ester
(Compound 2)

THERAPEUTIC COMPOSITION

RELATED APPLICATIONS

This application claims priority to U.S. Provisional Application No. 61/156,414, filed Feb. 27, 2009, and U.S. Provisional Application No. 61/257,367, filed Nov. 2, 2009, both of which are hereby incorporated by reference in their entireties.

BACKGROUND

1. Field

The present application relates to compositions and methods for the treatment of a disease condition such as a hepatitis C virus infection, liver fibrosis, and impaired liver function.

2. Description

Hepatitis C virus (HCV) infection is the most common chronic blood borne infection in the United States. Although the numbers of new infections have declined, the burden of chronic infection is substantial, with Centers for Disease Control estimates of 3.9 million (1.8%) infected persons in the United States. Chronic liver disease is the tenth leading cause of death among adults in the United States, and accounts for approximately 25,000 deaths annually, or approximately 1% of all deaths. Studies indicate that 40% of chronic liver disease is HCV-related, resulting in an estimated 8,000-10,000 deaths each year. HCV-associated end-stage liver disease is the most frequent indication for liver transplantation among adults.

Antiviral therapy of chronic hepatitis C has evolved rapidly over the last decade, with significant improvements seen in the efficacy of treatment. Nevertheless, even with using the standard of care (SOC) combination therapy of pegylated IFN-α plus ribavirin, 40% to 50% of patients fail therapy, i.e., are nonresponders or relapsers. These patients currently have no effective therapeutic alternative. In particular, patients who have advanced fibrosis or cirrhosis on liver biopsy are at significant risk of developing complications of advanced liver disease, including ascites, jaundice, variceal bleeding, encephalopathy, and progressive liver failure, as well as a markedly increased risk of hepatocellular carcinoma.

The high prevalence of chronic HCV infection has important public health implications for the future burden of chronic liver disease in the United States. Data derived from the National Health and Nutrition Examination Survey (NHANES III) indicate that a large increase in the rate of new HCV infections occurred from the late 1960s to the early 1980s, particularly among persons between 20 to 40 years of age. It is estimated that the number of persons with long-standing HCV infection of 20 years or longer could more than quadruple from 1990 to 2015, from 750,000 to over 3 million. The proportional increase in persons infected for 30 or 40 years would be even greater. Since the risk of HCV-related chronic liver disease is related to the duration of infection, with the risk of cirrhosis progressively increasing for persons infected for longer than 20 years, a substantial increase in cirrhosis-related morbidity and mortality is likely to result among patients infected between the years of 1965-1985.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins of the virus (NS2, NS3, NS4, NS4A, NS4B, NS5A, and NS5B).

SUMMARY

Some embodiments described herein relate to a composition that can include a first compound, or a pharmaceutically acceptable salt or prodrug thereof, wherein the first compound is β-D-2'-deoxy-2'-fluoro-2'-C-methylcytidine (Compound 1); and a second compound, or a pharmaceutically acceptable salt or prodrug thereof, wherein the second compound is (1S,4R,6S,14S,18R)-4-Fluoro-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.04,6]nonadec-7-en-18-yl ester (Compound 2).

Other embodiments described herein relate to a composition that consists essentially of a first compound, or a pharmaceutically acceptable salt or prodrug thereof, wherein the first compound is Compound 1; and a second compound, or a pharmaceutically acceptable salt or prodrug thereof, wherein the second compound is Compound 2.

An embodiment described herein relates to a method for ameliorating or treating a disease condition in a patient population that can include administering a therapeutically effective amount of a first compound, or a pharmaceutically acceptable salt or prodrug thereof, wherein the first compound is Compound 1; and a therapeutically effective amount of a second compound, or a pharmaceutically acceptable salt or prodrug thereof, wherein the second compound is Compound 2 to a subject suffering from the disease condition. In some embodiments, the disease condition can be selected from a hepatitis C virus infection, liver fibrosis, and impaired liver function. In an embodiment, the prodrug of the first compound can be the diisobutyl ester prodrug of β-D-2'-deoxy-2'-fluoro-2'-C-methylcytidine (Compound 1a). In some embodiments, the salt of the second compound can be the sodium salt of 1S,4R,6S,14S,18R)-4-Fluoro-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.04,6]nonadec-7-en-18-yl ester (sodium salt of Compound 2).

These and other embodiments are described in greater detail below.

DETAILED DESCRIPTION

Figure 1:
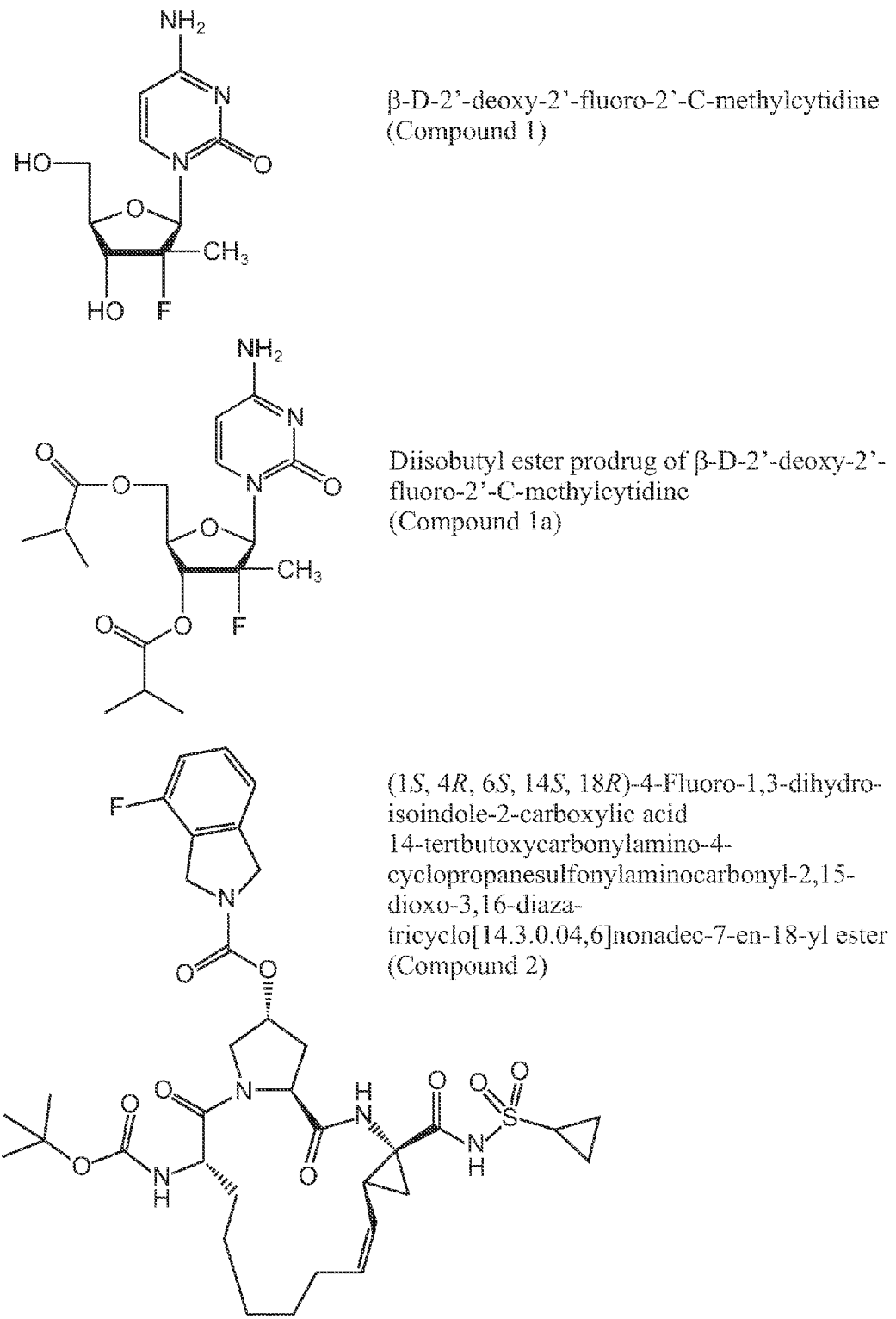
FIG. 1 shows the structures of β-D-2'-deoxy-2'-fluoro-2'-C-methylcytidine (Compound 1), the diisobutyl ester prodrug of β-D-2'-deoxy-2'-fluoro-2'-C-methylcytidine (Compound 1a) and (1S,4R,6S,14S,18R)-4-Fluoro-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.04,6]nonadec-7-en-18-yl ester (Compound 2).

Embodiments include, but are not limited to, therapeutic compositions and their use in the treatment and/or amelioration of a disease condition. In some embodiments, the disease condition can be selected from a hepatitis C virus infection, liver fibrosis, and/or impaired liver function.

Unless defined otherwise, all technical and scientific terms used herein have the same meaning as commonly understood by one of ordinary skill in the art to which the embodiments belong. All publications mentioned herein are incorporated herein by reference to disclose and describe the methods and/or materials in connection with which the publications are cited.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges, which may independently be included in the smaller ranges, are also encompassed within the invention, subject to any specifically excluded limit in the stated range. Where the stated range includes one or both of the limits, ranges excluding either or both of those included limits are also included in the embodiments.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like. The sodium salt of Compound 2 is a non-limiting example of a pharmaceutically acceptable salt.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Compound 1a is a non-limiting example of a prodrug (in this case a prodrug of Compound 1). Conventional procedures for the selection and preparation of suitable prodrug derivatives are described, for example, in *Design of Prodrugs*, (ed. H. Bundgaard, Elsevier, 1985), which is hereby incorporated herein by reference for the purpose of describing procedures and preparation of suitable prodrug derivatives.

The term "effective amount" is used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the symptoms of the disease being treated. Determination of an effective amount is well within the capability of those skilled in the art, especially in light of the detailed disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. In general, an effective amount of the compositions described herein, and optionally one or more additional antiviral agents, is an amount that is effective to reduce viral load or achieve a sustained viral response to therapy.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, murines, simians, humans, mammalian farm animals, mammalian sport animals, and mammalian pets.

As used herein, the term "hepatic fibrosis," used interchangeably herein with "liver fibrosis," refers to the growth of scar tissue in the liver that can occur in the context of a chronic hepatitis infection.

As used herein, the term "liver function" refers to a normal function of the liver, including, but not limited to, a synthetic function, including, but not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

The term "sustained viral response" (SVR; also referred to as a "sustained response" or a "durable response"), as used herein, refers to the response of an individual to a treatment regimen for HCV infection, in terms of serum HCV titer. For example, a "sustained viral response" refers to no detectable HCV RNA (e.g., less than about 500, less than about 200, or less than about 100 genome copies per milliliter serum) found in the patient's serum for a period of at least about one month, at least about two months, at least about three months, at least about four months, at least about five months, and/or at least about six months following cessation of treatment.

The compound, β-D-2'-deoxy-2'-fluoro-2'-C-methylcytidine (hereinafter "Compound 1") has been demonstrated to be effective in inhibiting HCV replication. Although this invention is not limited by any particular theory, it is believed that Compound 1 inhibits HCV replication by inhibiting the HCV RNA polymerase, an enzyme involved in the replication of the hepatitis C virus. Compound 1 can be obtained using methods known to those skilled in the art, such as those methods described in U.S. Pat. No. 7,419,572, which is hereby incorporated by reference in its entirety. Pharmaceutically acceptable salts and prodrugs of Compound 1 can be utilized in the compositions described herein. For example, the diisobutyl ester prodrug of β-D-2'-deoxy-2'-fluoro-2'-C-methylcytidine (Compound 1a), shown in FIG. 1, has been shown to have increased permeability that led to increased plasma exposure, and thereby improved anti-viral efficacy.

The compound, (1S,4R,6S,14S,18R)-4-Fluoro-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.04,6]nonadec-7-en-18-yl ester (hereinafter "Compound 2") has shown to be effective in inhibiting HCV replication. The aforementioned compound can be obtained using methods known to those skilled in the art, including, for example, those methods disclosed in U.S. Pat. No. 7,491,794, which is hereby incorporated by reference in its entirety. Although this invention is not limited by any particular theory, Compound 2 is believed to inhibit the HCV protease, in particular the NS3/4A protease. Pharmaceutically acceptable salts and prodrugs of Compound 2 can be utilized in the compositions described herein. For example, the sodium salt of Compound 2 can be included in compositions described herein. The structure and methods for producing the sodium salt are described in U.S. Publication No. 2007-0054842, filed on Jul. 21, 2006, which is hereby incorporated by reference in its entirety.

For the compounds described herein, each stereogenic carbon can be of R or S configuration. Although the specific compounds exemplified in this application can be depicted in a particular configuration, compounds having either the opposite stereochemistry at any given chiral center or mixtures thereof are also envisioned unless otherwise specified. When chiral centers are found in the salts or prodrugs of the compounds, it is to be understood that the compounds encompasses all possible stereoisomers unless otherwise indicated. In addition it is understood that, in any compound described herein having one or more double bond(s) generating geometrical isomers that can be defined as E or Z, each double bond may independently be E or Z a mixture thereof. Likewise, all tautomeric forms are also intended to be included.

Some embodiments described herein relate to a composition that can include Compound 1, or a pharmaceutically acceptable salt or prodrug thereof; and Compound 2, or a pharmaceutically acceptable salt or prodrug thereof. In an embodiment, the prodrug of Compound 1 can be Compound 1a. In some embodiments, the salt of Compound 2 can be the sodium salt.

An embodiment described herein relates to a composition consisting essentially of Compound 1, or a pharmaceutically acceptable salt or prodrug thereof; and Compound 2, or a pharmaceutically acceptable salt or prodrug thereof. In some embodiments, the prodrug of Compound 1 can be Compound 1a. In an embodiment, the salt of Compound 2 can be the sodium salt.

In some embodiments, the composition can further include a pharmaceutically acceptable excipient, diluent and/or carrier, such as those described herein.

Various amounts of Compound 1, or a pharmaceutically acceptable salt or prodrug thereof, can be included in the compositions described herein. In some embodiments, the composition can include an amount of Compound 1, or a pharmaceutically acceptable salt or prodrug thereof, in the range of about 9000 mg to about 50 mg. In other embodiments, the composition can include an amount of Compound 1, or a pharmaceutically acceptable salt or prodrug thereof, in the range of about 5000 mg to about 150 mg. In still other embodiments, the composition can include an amount of Compound 1, or a pharmaceutically acceptable salt or prodrug thereof, in the range of about 2000 mg to about 300 mg. In yet still other embodiments, the composition can include an amount of Compound 1, or a pharmaceutically acceptable salt or prodrug thereof, in the range of about 1000 mg to about 450 mg. In an embodiment, the composition can include an amount of Compound 1, or a pharmaceutically acceptable salt or prodrug thereof, in the range of about 1000 mg to about 500 mg.

Similarly, various amounts of Compound 2, or a pharmaceutically acceptable salt or prodrug thereof, can be included in the compositions. In some embodiments, the composition can include an amount of Compound 2, or a pharmaceutically acceptable salt or prodrug thereof, in the range of about 2000 mg to about 2 mg. In other embodiments, the composition can include an amount of Compound 2, or a pharmaceutically acceptable salt or prodrug thereof, in the range of about 1600 mg to about 25 mg. In still other embodiments, the composition can include an amount of Compound 2, or a pharmaceutically acceptable salt or prodrug thereof, in the range of about 500 mg to about 50 mg. In an embodiment, the composition can include an amount of Compound 2, or a pharmaceutically acceptable salt or prodrug thereof, in the range of about 200 mg to about 100 mg.

A potential advantage of utilizing a combination of Compounds 1 and 2, or pharmaceutically acceptable salts or prodrugs thereof, may be a reduction in the required amounts of one or more compounds that are effective in treating a disease condition disclosed herein (for example, HCV), as compared to monotherapy treatment of an otherwise comparable patient population using either Compound 1 or 2, or pharmaceutically acceptable salts or prodrugs thereof, alone. In some embodiments, the amount of Compound 1, or a pharmaceutically acceptable salt or prodrug thereof, in the composition can be less compared to the amount of Compound 1 or a pharmaceutically acceptable salt or prodrug thereof, needed to achieve the same viral load reduction when administered as a monotherapy. In some embodiments, the amount of Compound 2 or a pharmaceutically acceptable salt or prodrug thereof, in the composition can be less compared to the amount of Compound 2, or a pharmaceutically acceptable salt or prodrug thereof, needed to achieve the same viral load reduction when administered as a monotherapy. In an embodiment, the sum of the amount of Compound 1, or a pharmaceutically acceptable salt or prodrug thereof, and the amount of Compound 2, or a pharmaceutically acceptable salt or prodrug thereof, is less than expected or predicted based on the additive combination of Compound 1, or a pharmaceutically acceptable salt or prodrug thereof, alone and Compound 2, or a pharmaceutically acceptable salt or prodrug thereof, alone for treating the disease condition such as HCV.

Additional advantages of utilizing a combination of Compounds 1 and 2, or pharmaceutically acceptable salts or prodrugs thereof, may include little to no cross resistance between Compounds 1 and 2, or pharmaceutically acceptable salts or prodrugs thereof; different routes for elimination of Compounds 1 and 2, or pharmaceutically acceptable salts or prodrugs thereof; little to no overlapping toxicities between Compounds 1 and 2, or pharmaceutically acceptable salts or prodrugs thereof; little to no significant effects on cytochrome P450; and/or little to no pharmacokinetic interactions between Compounds 1 and 2, or pharmaceutically acceptable salts or prodrugs thereof.

The percentages of Compounds 1 and 2, or pharmaceutically acceptable salts or prodrugs thereof, present in the composition can also vary. For example, in some embodiments, the composition can include an amount of Compound 1, or a pharmaceutically acceptable salt or prodrug thereof, in the range of about 1% to about 99% (weight/weight) based on the sum of the amount of Compound 1, or a pharmaceutically acceptable salt or prodrug thereof, and the amount of Compound 2, or a pharmaceutically acceptable salt or prodrug thereof, in the composition. Additional embodiments include, but are not limited to, an amount of Compound 1, or a pharmaceutically acceptable salt or prodrug thereof, in the range of about 5% to about 90%, about 10% to about 80%, about 20% to about 70%, about 30% to about 60% and about 40% to about 50% (weight/weight) based on the sum of the amount of Compound 1, or a pharmaceutically acceptable salt or prodrug thereof, and the amount of Compound 2, or a pharmaceutically acceptable salt or prodrug thereof, in the composition. As to Compound 2, in an embodiment, the composition can include an amount of Compound 2, or a pharmaceutically acceptable salt or prodrug thereof, in the range of about 1% to about 99% (weight/weight) based on the sum of the amount of Compound 1, or a pharmaceutically acceptable salt or prodrug thereof, and the amount of Compound 2, or a pharmaceutically acceptable salt or prodrug thereof, in the composition. Examples of additional embodiments, include, but are not limited to, an amount of Compound 2, or a pharmaceutically acceptable salt or prodrug thereof, in the range of about 5% to about 90%, about 10% to about 80%, about 20% to about 70%, about 30% to about 60% and about 40% to about 50% (weight/weight) based on the sum of the amount of Compound 1, or a pharmaceutically acceptable salt or prodrug thereof, and the amount of Compound 2, or a pharmaceutically acceptable salt or prodrug thereof, in the composition.

Additional therapeutic agents can also be included in a composition that includes Compounds 1 and 2, or pharmaceutically acceptable salts or prodrugs thereof. In some embodiments, the additional therapeutic agent can be an anti-viral agent. In an embodiment, the anti-viral agent can be a HCV anti-viral agent. A non-limiting list of examples of suitable therapeutic agents include nucleotides and nucleoside analogs (such as azidothymidine (AZT) (zidovudine), and analogs and derivatives thereof; 2',3'-dideoxyinosine (DDI) (didanosine), and analogs and derivatives thereof; 2',3'-dideoxycytidine (DDC) (dideoxycytidine), and analogs and derivatives thereof; 2',3'-didehydro-2',3'-dideoxythymidine (D4T) (stavudine), and analogs and derivatives thereof; combivir; abacavir; adefovir dipivoxil; cidofovir; ribavirin; ribavirin analogs; levovirin, viramidine, isatoribine and the like), pirfenidone or a pirfenidone analogs, NS5B RNA-dependent RNA polymerase inhibitors, tumor necrosis factor antagonists (such as etanercept, infliximab and adalimumab), thymosin-α (Zadaxin™), an interferon receptor agonist(s), α-glucosidase inhibitors, TNF-α antagonists, NS3 helicase inhibitors, NS5B polymerase inhibitors, NS3 protease inhibitors (for example, (VX-950) and (SCH 503034)), Ritonavir (10-hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid, 5-thiazolylmethyl ester [5S-(5R*,8R*,10R*,11R*)], available from Abbott Laboratories), and ribozymes such as Heptazyme™ and phosphorothioate oligonucleotides which are complementary to HCV protein sequences and which inhibit the expression of viral core proteins.

One limitation of early interferon (IFN) therapy was rapid clearance of the protein from the blood. Chemical derivatization of IFN with polyethyleneglycol (PEG) has resulted in proteins with substantially improved pharmacokinetic properties. PEGASYS® is a conjugate of α-2a and a 40 kD branched mono-methoxy PEG and PEG-INTRON® is a conjugate of α-2b and a 12 kD mono-methoxy PEG. B. A. Luxon et al., *Clin. Therapy.* 2002, 24(9): 13631-1383; and A. Kozlowski and J. M Harris, *J. Control. Release,* 2001, 72: 217-224. However, some patients are unable or unwilling to subject themselves to interferon therapy for one or more reasons, for example, having to give themselves self-injections and/or one or more side effects related to interferon therapy. Compounds 1 and 2, or pharmaceutically acceptable salts or prodrugs thereof, further can include an interferon receptor agonist, such as a Type I interferon agonist and/or a Type II interferon agonist. In an embodiment, the Type II interferon agonist can be interferon-γ (IFN-γ). In an embodiment, the Type I interferon agonist can be interferon-α (IFN-α), for example, monoPEG (30 kD, linear)-ylate consensus, INFERGEN consensus IFN-α, a 40 kD branched mono-methoxy PEG conjugate of interferon α-2b and/or a 12 kD mono-methoxy PEG conjugate of interferon α-2b. In some embodiments, ribavirin can be also included in a composition that includes Compounds 1 and 2, or pharmaceutically acceptable salts or prodrugs thereof. In other embodiments, a composition that includes Compounds 1 and 2, or pharmaceutically acceptable salts or prodrugs thereof, does not include an interferon agonist. For example, the interferon agonist can be a Type I interferon agonist. In an embodiment, the Type I interferon agonist is a pegylated Type I interferon agonist such as those described herein. In still other embodiments, a composition that includes Compounds 1 and 2, or pharmaceutically acceptable salts or prodrugs thereof, does not include ribavirin.

As used herein, the term "interferon receptor agonist" refers to any Type I interferon receptor agonist, Type II interferon receptor agonist, or Type III interferon receptor agonist. As used herein, the term "a Type I interferon receptor agonist" refers to any naturally occurring or non-naturally occurring ligand of human Type I interferon receptor, which binds to and causes signal transduction via the receptor. Type I interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like. As used herein, the term "Type II interferon receptor agonist" refers to any naturally occurring or non-naturally occurring ligand of human Type II interferon receptor that binds to and causes signal transduction via the receptor. Type II interferon receptor agonists include native human interferon-γ, recombinant IFN-γ species, glycosylated IFN-γ species, pegylated IFN-γ species, modified or variant IFN-γ species, IFN-γ fusion proteins, antibody agonists specific for the receptor, non-peptide agonists, and the like. As used herein, the term "a Type III interferon receptor agonist" refers to any naturally occurring or non-naturally occurring ligand of humanIL-28 receptor α ("IL-28R"), the amino acid sequence of which is described by Sheppard, et al., infra., that binds to and causes signal transduction via the receptor.

Suitable α-glucosidase inhibitors include any of the above-described imino-sugars, including long-alkyl chain derivatives of imino sugars as disclosed in U.S. Patent Publication No. 2004/0110795; inhibitors of endoplasmic reticulum-associated α-glucosidases; inhibitors of membrane bound α-glucosidase; miglitol (Glyset®), and active derivatives, and analogs thereof; and acarbose (Precose®), and active derivatives, and analogs thereof.

The compositions described herein can be administered to a human patient per se, or in compositions where they are mixed with other active ingredients, as in combination therapy, or carriers, diluents, excipients or combinations thereof, and may be formulated into preparations in solid, semi-solid, liquid or gaseous forms, such as tablets, capsules, powders, granules, ointments, solutions, suppositories, injections, inhalants and aerosols. Proper formulation is dependent upon the route of administration chosen. Techniques for formulation and administration of the compositions described herein are known to those skilled in the art. Pharmaceutically acceptable excipients are known to those skilled in the art, and are described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the compositions disclosed herein may be provided as salts with pharmaceutically compatible counterions.

In some embodiments, the compounds, or pharmaceutically acceptable salts or prodrugs thereof, (e.g., Compounds 1, 1a and 2) are formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

Suitable routes of administration may, for example, include oral, rectal, topical transmucosal, or intestinal administration; parenteral delivery, including intramuscular, subcutaneous, intravenous, intramedullary injections, as well as intrathecal, direct intraventricular, intraperitoneal, intranasal, intraocular injections or as an aerosol inhalant. The compositions will generally be tailored to the specific intended route of administration. In an embodiment, the compositions described herein can be administered orally.

Subcutaneous administration can be accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a pharmaceutical composition of the embodiments to a patient through the port is referred to herein as "a subcutaneous injection port delivery system." In many embodiments, subcutaneous administration is achieved by bolus delivery by needle and syringe.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the embodiments can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the embodiments calculated in an amount sufficient to produce the desired effect in association with a pharmaceutically acceptable diluent, carrier or vehicle. The specifications for the novel unit dosage forms of the embodiments depend on the particular compound employed and the effect to be achieved, and the pharmacodynamics associated with each compound in the host.

The compositions described herein can be administered orally, parenterally or via an implanted reservoir. In an embodiment, the composition can be orally administered or administered by injection.

One may also administer the composition in a local rather than systemic manner, for example, via injection of the composition directly into the infected area, often in a depot or sustained release formulation. Furthermore, one may administer the composition in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

Some embodiments described herein relate to a method for ameliorating or treating a disease condition that can include administering an amount of Compound 1, or a pharmaceutically acceptable salt or prodrug thereof, and an amount of Compound 2, or a pharmaceutically acceptable salt or prodrug thereof, wherein the disease condition can be a hepatitis C virus infection, liver fibrosis, and/or impaired liver function. In an embodiment, the prodrug of Compound 1 can be Compound 1a.

Various dosages forms of Compound 1, or a pharmaceutically acceptable salt or prodrug thereof, and/or Compound 2, or a pharmaceutically acceptable salt or prodrug thereof, can be used to ameliorate and/or treat a disease condition. In some instances, Compounds 1 and 2, or pharmaceutically acceptable salts or prodrugs thereof, can be present in the same dosage form such as the compositions described herein. In other instances, Compounds 1 and 2, or pharmaceutically acceptable salts or prodrugs thereof, can be administered as separate dosage forms. For example, Compound 1, or a pharmaceutically acceptable salt or prodrug thereof, can be administered in one tablet and Compound 2, or a pharmaceutically acceptable salt or prodrug thereof, can be administered in a second tablet. When Compounds 1 and 2, or pharmaceutically acceptable salts or prodrugs thereof, are contained in separate dosage forms, the dosage forms can be the same (e.g., as both pills) or different (e.g., one compound can be formulated in a pill and the other compound can be formulated as an injectable).

Administration of Compound 1, or a pharmaceutically acceptable salt or prodrug thereof, and Compound 2, or a pharmaceutically acceptable salt or prodrug thereof, can vary. When Compounds 1 and 2, or pharmaceutically acceptable salts or prodrugs thereof, are contained in separate dosage forms, the dosage forms can be administered simultaneously or sequentially. In some embodiments, the dosage form that contains Compound 1, or a pharmaceutically acceptable salt or prodrug thereof, can be administered before the dosage form that contains Compound 2, or a pharmaceutically acceptable salt or prodrug thereof. In other embodiments, the dosage form that contains Compound 1, or a pharmaceutically acceptable salt or prodrug thereof, can be administered after the dosage form that contains Compound 2, or a pharmaceutically acceptable salt or prodrug thereof. In still other embodiments, the dosage form that contains Compound 1, or a pharmaceutically acceptable salt or prodrug thereof, can be administered at approximately the same time as the dosage form that contains Compound 2, or a pharmaceutically acceptable salt or prodrug thereof.

In some embodiments, Compounds 1 and 2, or pharmaceutically acceptable salts or prodrugs thereof, can be administered concurrently. As used, the term "concurrently" means effective concentrations of both compounds are present in a subject. When being administered concurrently, Compounds 1 and 2, or pharmaceutically acceptable salts or prodrugs thereof, can be administered in the same dosage form or separate dosage forms. In other embodiments, Compounds 1 and 2, or pharmaceutically acceptable salts or prodrugs thereof, can be administered sequentially. As used herein, the term "sequentially" means administering one compound for a first time period and then administering a second compound for a second time period in which the first and second time periods do not overlap.

Additional therapeutic agents can also be administered to the subject having the disease condition. A non-limiting list of additional therapeutic agents includes those previously described herein. When one or more additional therapeutic agents are utilized, the additional agent(s) can be administered in the same dosage form as Compound 1, or a pharmaceutically acceptable salt or prodrug thereof, and/or Compound 2, or a pharmaceutically acceptable salt or prodrug thereof. For example, the additional therapeutic agent(s) can be included in a composition that includes Compound 1, or a pharmaceutically acceptable salt or prodrug thereof, without Compound 2, or a pharmaceutically acceptable salt or prodrug thereof; or a composition that includes Compound 2, or a pharmaceutically acceptable salt or prodrug thereof, without Compound 1, or a pharmaceutically acceptable salt or prodrug thereof; or a composition described herein (for example, a composition that includes Compounds 1 and 2, or pharmaceutically acceptable salts or prodrugs thereof). Alternatively, the additional therapeutic agent(s) can be administered in one or more separate dosage forms. If administered as one or more separate dosage forms, each dosage form with one or more additional therapeutic agents can be the same as the dosage form containing Compound 1, or a pharmaceutically acceptable salt or prodrug thereof, and/or the dosage form containing Compound 2, or a pharmaceutically acceptable salt or prodrug thereof, or different from the dosage form containing Compound 1, or a pharmaceutically acceptable salt or prodrug thereof, and/or the dosage form containing Compound 2, or a pharmaceutically acceptable salt or prodrug thereof.

When one or more additional therapeutic agents are in one or more separate dosage forms, the dosage forms with one or more additional therapeutic agents can be administered before, after, in-between, concurrently or sequentially with Compound 1, or a pharmaceutically acceptable salt or prodrug thereof, and/or Compound 2, or a pharmaceutically acceptable salt or prodrug thereof. In some embodiments, the additional therapeutic agent can be an interferon receptor agonist, for example, a Type I interferon receptor agonist and/or a Type II interferon receptor agonist. In an embodiment, the Type II interferon agonist can be interferon-γ (IFN-γ). In an embodiment, the Type 1 interferon agonist can be interferon-α (IFN-α). In some embodiments, the Type I interferon agonist can be selected from monoPEG (30 kD, linear)-ylate consensus, INFERGEN consensus IFN-α, a 40 kD branched mono-methoxy PEG conjugate of interferon α-2b and a 12 kD mono-methoxy PEG conjugate of interferon α-2b. In an embodiment, the additional therapeutic agent can be ribavirin. In some embodiments, Compounds 1 and 2 can be administered without administering one or more additional therapeutic agents such as an interferon receptor agonist and/or ribavirin. In an embodiment, the interferon receptor agonist can be a Type 1 interferon receptor agonist, such as a pegylated Type 1 interferon receptor agonist.

One or more additional therapeutic agents can be administered after administration of Compound 1, or a pharmaceutically acceptable salt or prodrug thereof, and Compound 2, or a pharmaceutically acceptable salt or prodrug thereof. For example, one or more additional therapeutic agents can be administered after completion of a treatment regimen with Compound 1, or a pharmaceutically acceptable salt or prodrug thereof, and Compound 2, or a pharmaceutically acceptable salt or prodrug thereof. In some embodiments, the additional therapeutic agent can be an interferon receptor agonist such as a Type I interferon receptor agonist. In an embodiment, the Type I interferon receptor agonist can be a pegylated Type I interferon receptor agonist. In some embodiments, the additional therapeutic agent can be ribavirin.

Whether a subject method is effective in treating an HCV infection can be determined in various ways, for example, by a reduction in viral load, a reduction in time to seroconversion (virus undetectable in patient serum), an increase in the rate of sustained viral response to therapy, a reduction of morbidity or mortality in clinical outcomes, or other indicator of disease response. Thus, whether a subject method is effective in treating an HCV infection can be determined by measuring viral load, or by measuring a parameter associated with HCV infection, including, but not limited to, liver fibrosis, elevations in serum transaminase levels, and necroinflammatory activity in the liver.

In some embodiments, administration and/or use of Compounds 1 and 2, or pharmaceutically acceptable salts or prodrugs thereof, in combination can reduce the viral load more than the viral load reduction achieved by administration of Compound 1, or a pharmaceutically acceptable salt or prodrug thereof, alone at substantially the same amount. For example, the combination of Compounds 1 and 2, or pharmaceutically acceptable salts or prodrugs thereof, may reduce the viral load by at least about 10%, at least about 15%, at least about 20%, at least about 25%, at least about 30%, at least about 40%, at least about 50%, at least about 60%, at least about 70%, at least about 80%, or at least about 90%, or more, as compared to the reduction of HCV viral load achieved by substantially the same amount of Compound 1, or a pharmaceutically acceptable salt or prodrug thereof, administered as a monotherapy. In some embodiments, administration and/or use of Compounds 1 and 2, or pharmaceutically acceptable salts or prodrugs thereof, in combination can reduce the viral load more than the viral load reduction achieved by the administration of substantially the same amount of Compound 2, or a pharmaceutically acceptable salt or prodrug thereof, alone. As examples, the combination of Compounds 1 and 2, or pharmaceutically acceptable salts or prodrugs thereof, may reduce the viral load by at least about 10%, at least about 15%, at least about 20%, at least about 25%, at least about 30%, at least about 40%, at least about 50%, at least about 60%, at least about 70%, at least about 80%, or at least about 90%, or more, as compared to the reduction of HCV viral load achieved by substantially the same amount of Compound 2, or a pharmaceutically acceptable salt or prodrug thereof, administered as a monotherapy.

In some embodiments, an amount of Compound 1, or a pharmaceutically acceptable salt or prodrug thereof, and an amount of Compound 2, or a pharmaceutically acceptable salt or prodrug thereof, is a synergistic amount. As used herein, a "synergistic combination" or a "synergistic amount" is a combined dosage that is more effective in the therapeutic or prophylactic treatment of an HCV infection than the incremental improvement in treatment outcome that could be predicted or expected from a merely additive combination of (i) the therapeutic or prophylactic benefit of Compound 1, or a pharmaceutically acceptable salt or prodrug thereof, when administered at that same dosage as a monotherapy and (ii) the therapeutic or prophylactic benefit of Compound 2, or a pharmaceutically acceptable salt or prodrug thereof, when administered at the same dosage as a monotherapy. The term "synergistic combination" or a "synergistic amount" may also be used to refer to a combined dosage that is more effective in the therapeutic or prophylactic treatment of an HCV infection than could be predicted or expected, based on the rule of mixtures, from a combination of (i) the therapeutic or prophylactic benefit of Compound 1, or a pharmaceutically acceptable salt or prodrug thereof, and (ii) the therapeutic or prophylactic benefit of Compound 2, or a pharmaceutically acceptable salt or prodrug thereof. Accordingly, in some embodiments, the combination of Compounds 1 and 2, or pharmaceutically acceptable salts or prodrugs thereof, may reduce the viral load by at least about 10%, at least about 15%, at least about 20%, at least about 25%, at least about 30%, at least about 40%, at least about 50%, at least about 60%, at least about 70%, at least about 80%, or at least about 90%, or more, as compared to the reduction in HCV viral load predicted or expected from the rule of mixtures or additive combination of the viral load reductions from administration of Compound 1, or a pharmaceutically acceptable salt or prodrug thereof, and Compound 2, or a pharmaceutically acceptable salt or prodrug thereof. In some embodiments, the foregoing levels of viral load reduction are averages based on a population of subjects. HCV viral load and viral load reduction can be determined by methods known in the art. For example, HCV viral load may be determined by measuring HCV RNA levels using a suitable assay such as a reverse transcriptase PCR assay. In one embodiment, the assay is the COBAS® AmpilPrep/COBAS® Taqman® HCV Test RUO.

The combination of Compounds 1 and 2, or pharmaceutically acceptable salts or prodrugs thereof, may shorten the time period it takes a subject to achieve a sustained viral response to therapy. For example, the combination of Compounds 1 and 2, or pharmaceutically acceptable salts or prodrugs thereof, may shorten the time period it takes a subject to achieve a sustained viral response to therapy compared to the time period it takes the subject to achieve a sustained viral response being administered substantially the same amount of Compound 1, or a pharmaceutically acceptable salt or prodrug thereof, as a monotherapy. Likewise or in the alternative, the combination of Compounds 1 and 2, or pharmaceutically acceptable salts or prodrugs thereof, may shorten the time period it takes a subject to achieve a sustained viral response to therapy compared to the time period it takes the subject to achieve a sustained viral response to therapy being administered substantially the same amount of Compound 2, or a pharmaceutically acceptable salt or prodrug thereof, as a monotherapy. In an embodiment, the combination of Compounds 1 and 2, or pharmaceutically acceptable salts or prodrugs thereof, may shorten the time period it takes a subject to achieve a sustained viral response to therapy by at least about 10%, at least about 15%, at least about 20%, at least about 25%, at least about 30%, at least about 40%, at least about 50%, at least about 60%, at least about 70%, at least about 80%, or at least about 90%, or more, as compared to that expected based on the rule of mixtures or additive combination expected or predicted from the time period it takes the subject to achieve a sustained viral response to therapy being administered substantially the same amount of Compound 1, or a pharmaceutically acceptable salt or prodrug thereof, as monotherapy and the time period it takes the subject to achieve a sustained viral response to therapy being administered substantially the same amount of Compound 2, or a pharmaceutically acceptable salt or prodrug thereof, as monotherapy. In some embodiments, the time periods for achieving a sustained viral response are averages based on a population of subjects.

As noted above, whether a subject method is effective in treating an HCV infection can be determined by measuring a parameter associated with HCV infection, such as liver fibrosis. Methods of determining the extent of liver fibrosis are known to those skilled in the art. In some embodiments, the level of a serum marker of liver fibrosis indicates the degree of liver fibrosis.

As a non-limiting example, levels of serum alanine aminotransferase (ALT) are measured, using standard assays. In general, an ALT level of less than about 45 international units is considered normal. In some embodiments, the combination of Compounds 1 and 2, or pharmaceutically acceptable salts or prodrugs thereof, reduces a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in a subject undergoing monotherapy (such as being administered substantially the same amount of Compound 1 or 2, or a pharmaceutically acceptable salt or prodrug thereof, alone). In other embodiments, the combination of Compounds 1 and 2, or pharmaceutically acceptable salts or prodrugs thereof, reduces a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, as compared to that expected based on the rule of mixtures or the additive combination of the levels of reduction of a serum level of a marker of liver fibrosis using substantially the same amounts of Compounds 1 and 2, or pharmaceutically acceptable salts or prodrugs thereof. In some embodiments, the reduction of serum levels of a marker of liver fibrosis are averages based on a population of subjects.

A subject being treated for a disease condition can experience resistance to one or more of the therapeutic agents (for example, Compound 1, or a pharmaceutically acceptable salt or prodrug thereof, and/or Compound 2, or a pharmaceutically acceptable salt or prodrug thereof). The term "resistance" as used herein refers to a subject displaying a delayed, lessened and/or absent response to the therapeutic agent(s). For example, the viral load of a subject with HCV who has become resistant to an anti-viral or combination thereof may be reduced to a lesser degree compared to the amount in viral load reduction exhibited by the subject before becoming resistant to the anti-viral or combination thereof and/or the determined normal mean viral load reduction. In some embodiments, the level of resistance of the disease condition to therapy can be decreased compared to the level of resistance measured in a subject being administered substantially the same amount of Compound 1, or a pharmaceutically acceptable salt or prodrug thereof, as a monotherapy. In some embodiments, the level of resistance of the disease condition to therapy can be decreased compared to the level of resistance measured in a subject being administered substantially the same amount of Compound 2, or a pharmaceutically acceptable salt or prodrug thereof, as a monotherapy. In other embodiments, the combination of Compounds 1 and 2, or pharmaceutically acceptable salts or prodrugs thereof, reduces the level of resistance of the disease condition to therapy by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, as compared to that expected based on the rule of mixtures or additive combination of the levels of resistance using substantially the same amounts of Compounds 1 and 2, or pharmaceutically acceptable salts or prodrugs thereof. In some embodiments, the levels of resistance are averages based on a population of subjects.

Some subjects being treated for HCV who develop or have resistance for one or more therapies experience a viral load rebound. The term "viral load rebound" as used herein refers to a sustained ≥0.5 log IU/ml increase of viral load above nadir before the end of treatment, where nadir is a ≥0.5 log IU/ml decrease from baseline. In some embodiments, co-administration of Compound 1, or pharmaceutically acceptable salts or prodrugs thereof, and Compound 2, or pharmaceutically acceptable salts or prodrugs thereof, results in less subjects experiencing a viral load rebound as compared to monotherapy with Compound 1, or a pharmaceutically acceptable salt or prodrug thereof, or Compound 2, or a pharmaceutically acceptable salt or prodrug thereof. In some embodiments, the co-administration of Compounds 1 and 2, or pharmaceutically acceptable salts or prodrugs thereof, results in at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, reduction in number of subjects experiencing a viral load rebound as compared to monotherapy, for example monotherapy with Compound 1, or pharmaceutically acceptable salts or prodrugs thereof, and Compound 2, or pharmaceutically acceptable salts or prodrugs thereof. In some embodiments, the co-administration of Compounds 1 and 2, or pharmaceutically acceptable salts or prodrugs thereof, results in less than about 75%, less than about 50%, less than about 40%, less than about 30%, less than about 20%, less than about 10%, or less than about 5% of the patient population who experiences a viral load rebound. In other embodiments, the combination of Compounds 1 and 2, or pharmaceutically acceptable salts or prodrugs thereof, reduces the percentage of the patient population who experiences a viral load rebound by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, as compared to that expected based on the rule of mixtures.

Some subjects being treated for HCV who develop or have resistance for one or more therapies are or become non-responders. The term "non-responder" as used herein refers to a viral load decrease ≤0.5 log IU/ml during treatment. In some embodiments, co-administration of Compound 1, or a pharmaceutically acceptable salt or prodrug thereof, and Compound 2, or a pharmaceutically acceptable salt or prodrug thereof, results in less subjects who are non-responders as compared to monotherapy of Compound 1, or a pharmaceutically acceptable salt or prodrug thereof, or Compound 2, or a pharmaceutically acceptable salt or prodrug thereof. In some embodiments, the co-administration of Compounds 1 and 2, or pharmaceutically acceptable salts or prodrugs thereof, results in at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, reduction in number of patients who are non-responders as compared to monotherapy. In some embodiments, the co-administration of Compounds 1 and 2, or pharmaceutically acceptable salts or prodrugs thereof, results in less than about 75%, less than about 50%, less than about 40%, less than about 30%, less than about 20%, less than about 10%, or less than about 5% of the patient population who are non-responders. In other embodiments, the combination of Compounds 1 and 2, or of pharmaceutically acceptable salts or prodrugs thereof, reduces the percentage of the patient population who are non-responders by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, as compared to that expected based on the rule of mixtures.

In addition or in the alternative, in some embodiments, the onset of resistance of the disease condition to therapy can be delayed compared to when the onset of resistance occurs in a subject being administered substantially the same amount of Compound 1, or a pharmaceutically acceptable salt or prodrug thereof, as a monotherapy. In some embodiments, the onset of resistance of the disease condition to therapy can be delayed compared to when the onset of resistance occurs in a subject being administered substantially the same amount of Compound 2, or a pharmaceutically acceptable salt or prodrug thereof, as a monotherapy. In an embodiment, Compound 1, or a pharmaceutically acceptable salt or prodrug thereof, can delay the onset of resistance to Compound 2, or a pharmaceutically acceptable salt or prodrug thereof. For example, Compound 1, or a pharmaceutically acceptable salt or prodrug thereof, can delay the onset of HCV resistance to Compound 2, or a pharmaceutically acceptable salt or prodrug thereof, as indicated by an HCV replicon assay. As used herein, the phrase "onset of resistance" is the point in time when the subject shows resistance to one or more therapeutic compounds. In an embodiment, the disease can be HCV. In some embodiments, the combination of Compounds 1 and 2, or of pharmaceutically acceptable salts or prodrugs thereof, may be a synergistic combination in that the onset of resistance may be delayed by at least about 10%, at least about 15%, at least about 20%, at least about 25%, at least about 30%, at least about 40%, at least about 50%, at least about 60%, at least about 70%, at least about 80%, or at least about 90%, or more, as compared to when the onset of resistance is predicted or expected based on the rule of mixtures or the additive combination of substantially the same amounts of Compounds 1 and 2, or pharmaceutically acceptable salts or prodrugs thereof. In some embodiments, the time of the onset of resistance is an average based on a population of subjects.

Often one or more side effects are experienced by subjects being treated with therapeutic agents such as anti-viral compounds. In some instances, the side effects may be to such a degree that treatment with the agent may not be feasible or recommended such that treatment is not an option for some subjects or treatment has to be stopped. By lessening or decreasing the number and/or severity of the side effects, subject compliance with the treatment may be increased. In some embodiments, the number of side effects associated with co-administration of Compound 1, or a pharmaceutically salt or prodrug thereof; and Compound 2, or a pharmaceutically acceptable salt or prodrug thereof, can be less than the number of side effects exhibited by the subject being administered substantially the same amount of Compound 1, or a pharmaceutically acceptable salt or prodrug thereof, as the only active agent. In some embodiments, the number of side effects associated with co-administration of Compound 1, or a pharmaceutically salt or prodrug thereof, and Compound 2, or a pharmaceutically acceptable salt or prodrug thereof can be less than the number of side effects exhibited by the subject being administered substantially the same amount of Compound 2, or a pharmaceutically acceptable salt or prodrug thereof, as the only active agent. In other embodiments, the subject being administered a combination of Compounds 1 and 2, or pharmaceutically acceptable salts or prodrugs thereof, may exhibit less side effects than predicted or expected based on the rule of mixtures or the additive combination of side effects experienced by a subject being administered substantially the same amounts of Compounds 1 and 2, or pharmaceutically acceptable salts or prodrugs thereof, by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%. In some embodiments, the number of side effects is an average based on a population of subjects.

As previously stated, compliance by subjects to the antiviral treatment may also be increased by decreasing the severity of one or more side effects that is associated with monotherapy with the active compounds. In some embodiments, the severity of a side effect associated with the combination of Compound 1, or a pharmaceutically acceptable salt or prodrug thereof, and Compound 2, or a pharmaceutically acceptable salt or prodrug thereof, is decreased compared to the severity of the side effect experienced by the subject being administered Compound 1, or a pharmaceutically acceptable salt or prodrug thereof, as a monotherapy. In an embodiment, the severity of a side effect associated with the combination of Compound 1, or a pharmaceutically acceptable salt or prodrug thereof, and Compound 2, or a pharmaceutically acceptable salt or prodrug thereof, is decreased compared to the severity of the side effect experienced by the subject being administered Compound 2, or a pharmaceutically acceptable salt or prodrug thereof, as a monotherapy. In some embodiments, the severity of a side effect associated with the combination of Compound 1, or a pharmaceutically acceptable salt or prodrug thereof, and Compound 2, or a pharmaceutically acceptable salt or prodrug thereof, may be decreased by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, as compared to the severity of the side effect predicted or expected based on the rule of mixtures or the additive combination of the severities of the side effect associated with substantially the same amount of Compound 1, or a pharmaceutically acceptable salt or prodrug thereof, and substantially the same amount of Compound 2, or a pharmaceutically acceptable salt or prodrug thereof. In some embodiments, the severity of a side effect is an average based on a population of subjects.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. (See e.g., Fingl et al. 1975, in "The Pharmacological Basis of Therapeutics", which is hereby incorporated herein by reference in its entirety, with particular reference to Ch. 1, p. 1). The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

Although the exact dosage will be determined on a drug-by-drug basis, in most cases, some generalizations regarding the dosage can be made. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages, or dosages that are between about 0.1% and 500%, more preferably between about 25% and 250% of the established human dosage will be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response was not adequate (precluding toxicity). The magnitude of an administered dose in the management of the disorder of interest will vary with the severity of the condition to be treated and the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Alternatively dosages may be based and calculated upon the surface area of the patient, as understood by those of skill in the art.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound or composition in humans.

Any of the compositions and methods described herein can be administered to individuals who have been diagnosed with an HCV infection. Any of the compositions and methods described herein can be administered to individuals who have failed previous treatment for HCV infection ("treatment failure patients," including non-responders and relapsers).

Individuals who have been clinically diagnosed as infected with HCV are of particular interest in many embodiments. Individuals who are infected with HCV are identified as having HCV RNA in their blood, and/or having anti-HCV antibody in their serum. Such individuals include anti-HCV ELISA-positive individuals, and individuals with a positive recombinant immunoblot assay (RIBA). Such individuals may also, but need not, have elevated serum ALT levels.

Individuals who are clinically diagnosed as infected with HCV include naïve individuals (e.g., individuals not previously treated for HCV, particularly those who have not previously received IFN-α-based and/or ribavirin-based therapy) and individuals who have failed prior treatment for HCV ("treatment failure" patients). Treatment failure patients include non-responders (i.e., individuals in whom the HCV titer was not significantly or sufficiently reduced by a previous treatment for HCV, e.g., a previous IFN-α monotherapy, a previous IFN-α and ribavirin combination therapy, or a previous pegylated IFN-α and ribavirin combination therapy); and relapsers (i.e., individuals who were previously treated for HCV, e.g., who received a previous IFN-α monotherapy, a previous IFN-α and ribavirin combination therapy, or a previous pegylated IFN-α and ribavirin combination therapy, whose HCV titer decreased, and subsequently increased).

In an embodiment, HCV-positive individuals have an HCV titer of at least about $10^5$, at least about $5 \times 10^5$, or at least about $10^6$, or at least about $2 \times 10^6$, genome copies of HCV per milliliter of serum. The patient may be infected with any HCV genotype (genotype 1, including 1a and 1b, 2, 3, 4, 6, etc. and subtypes (e.g., 2a, 2b, 3a, etc.)), particularly a difficult to treat genotype such as HCV genotype 1 and particular HCV subtypes and quasispecies.

In some embodiments, the HCV-positive individuals (as described above) are those who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment with IFN-α-based therapies or who cannot tolerate IFN-α-based therapies, or who have a contraindication to such therapies. In an embodiment, HCV-positive individuals with stage 3 or 4 liver fibrosis according to the METAVIR scoring system are suitable for treatment with the compositions and methods described herein. In other embodiments, individuals suitable for treatment with the compositions and methods described herein are patients with decompensated cirrhosis with clinical manifestations, including patients with far-advanced liver cirrhosis, including those awaiting liver transplantation. In still other embodiments, individuals suitable for treatment with the compositions and methods described herein include patients with milder degrees of fibrosis including those with early fibrosis (stages 1 and 2 in the METAVIR, Ludwig, and Scheuer scoring systems; or stages 1, 2, or 3 in the Ishak scoring system).

EXAMPLES

Embodiments are disclosed in further detail in the following examples, which are not in any way intended to limit the scope of the claims.

Example 1

Treatment Protocols

A randomized, double-blind, placebo controlled, dose ranging study of Compound 1a and Compound 2 in adult patients with chronic hepatitis C genotype 1 was conducted. Approximately 54 treatment naïve males and females between 18 and 65 years of age (inclusive) with genotype 1 HCV infection who had not previously been treated with an interferon or investigational HCV therapeutic agent were enrolled. Approximately an additional 20 treatment patients who had failed treatment with the current standard of care (null, partial responders and relapsers) were enrolled. Subjects had a liver biopsy or non-invasive (e.g., Fibroscan) procedure within 24 calendar months of first dose consistent with chronic hepatitis C without cirrhosis. Liver biopsies within 5 years demonstrating F0 or F1 disease were also acceptable. Subjects with liver cirrhosis or incomplete/transition to cirrhosis, or other forms of liver disease, anemia, HIV or HBV infection, hepatocellular carcinoma, cardiac disease or renal disease were excluded from this particular protocol, as well as pregnant or lactating women, women of childbearing potential, and male partners of women who are pregnant or lactating. Women of non-child bearing potential is defined as post-menopausal (not had a spontaneous menstrual period for at least 1 year and confirmation by FSH and LH laboratory results); surgical sterile (status post hysterectomy or tubal ligation for at least 6 months); and/or, natural sterile (amenorrheic for at least 1 year).

Seven groups, Groups I, II, III, IV, V, VI and VII, of subjects were studied. Blood samples were collected at time points to determine pharmacokinetics parameters, including $T_{max}$, $C_{max}$, $K_{el}$, $T_{1/2}$, AUC, CL/F, Vd/F and accumulation ratio.

Figure 2:
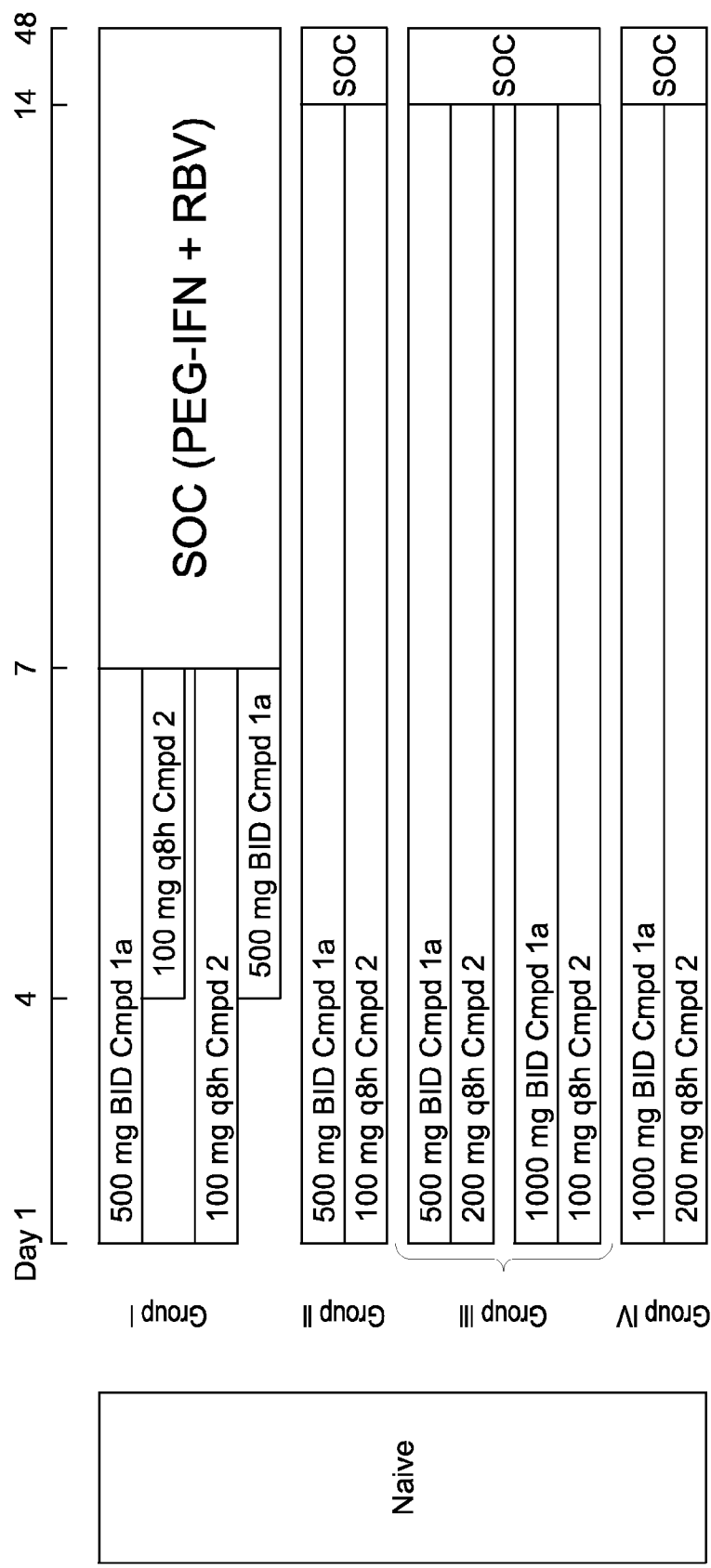
FIGS. 2 and 3 show a pictorial representation of seven treatment regimes using the compounds shown in FIG. 1.
Figure 3:
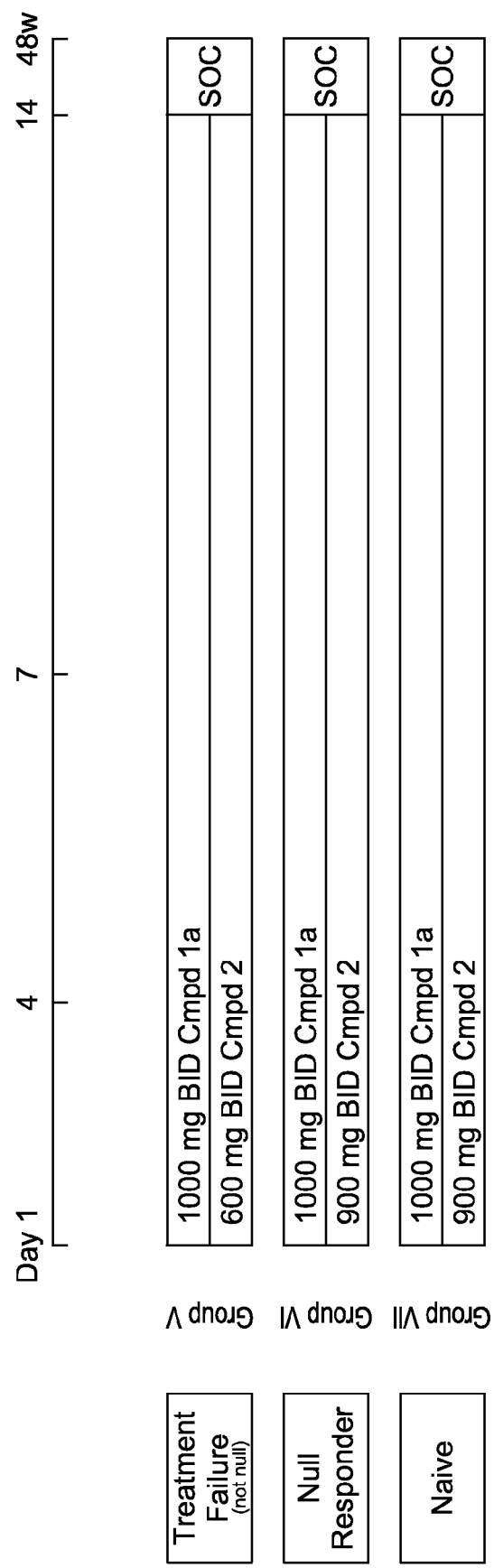

The specifics of Groups I, II, III, IV, V, VI and VII are shown in Table 1 below and pictorially in FIGS. 2 and 3. Group I included two arms with 8 subjects in Arm 1 and 8 subjects in Arm 2. In Arm 1, Compound 1a was administered for the full 7 days and Compound 2 was administered for the last half of the seven days. In Arm 2, Compound 2 was administered the full seven days and Compound 1a was administered the last half of the seven days. For Group H, a total of 10 subjects were enrolled. The subjects were either receiving Compounds 1a and 2, or placebos for the full fourteen days. Group I and Group II were completed sequentially.

For Groups III and IV, subjects received Compounds 1a and 2, or placebos for the full fourteen days. Group III enrolled 18 subjects which were administered either 500 mg (Compound 1a) and 200 mg (Compound 2), 1000 mg (Compound 1a) and 100 mg (Compound 2), or placebos of Compounds 1a and 2. Group IV enrolled 12 subjects. 8 subjects in Group IV took 1000 mg (Compound 1a) and 200 mg (Compound 2), and 4 subjects took placebos. Groups III and IV were completed sequentially after the safety data for Groups I and II was obtained.

For Groups V, VI and VII, subjects received Compounds 1a and 2 or placebos for the full fourteen days. Group V enrolled 10 subjects who were classified as treatment failure non-null. Eight subjects in Group V took 1000 mg (Compound 1a) and 600 mg (Compound 2), and 2 subjects in Group V took placebos of Compounds 1a and 2. Group VI enrolled 10 subjects classified as treatment null. Eight subjects in Group VI were administered 1000 mg (Compound 1a) and 900 mg (Compound 2), and 2 subjects were administered placebos of Compounds 1a and 2. Group VII enrolled 10 subjects. Eight subjects in Group VII took 1000 mg (Compound 1a) and 900 mg (Compound 2), and 2 subjects in Group VII took placebos of Compounds 1a and 2.

TABLE 1

| Group | Compound | Amount | Frequency | Regime |
|---|---|---|---|---|
| I Arm 1 | 1a | 500 mg | bid | Days 1 to 7 |
| (n = 8) | 2 placebo | NA | q8h | Days 1 to 3 |
|  | 2 | 100 mg | q8h | Days 4 to 7 |
| I Arm 2 | 2 | 100 mg | q8h | Days 1 to 7 |
| (n = 8) | 1a placebo | NA | bid | Days 1 to 3 |
|  | 1a | 500 mg | bid | Days 4 to 7 |
| II Arm 1 | 1a | 500 mg | bid | Days 1 to 14 |
| (n = 8) | 2 | 100 mg | q8h | Days 1 to 14 |
| II Arm 2 | 1a placebo | NA | bid | Days 1 to 14 |
| (n = 2) | 2 placebo | NA | q8h | Days 1 to 14 |
| III Arm 1 | 1a | 500 mg | bid | Days 1 to 14 |
| (n = 8) | 2 | 200 mg | q8h | Days 1 to 14 |
| III Arm 2 | 1a | 1000 mg | bid | Days 1 to 14 |
| (n = 8) | 2 | 100 mg | q8h | Days 1 to 14 |
| III Arm 3 | 1a placebo | NA | bid | Days 1 to 14 |
| (n = 2) | 2 placebo | NA | q8h | Days 1 to 14 |
| IV Arm 1 | 1a | 1000 mg | bid | Days 1 to 14 |
| (n = 8) | 2 | 200 mg | q8h | Days 1 to 14 |
| IV Arm 2 | 1a placebo | NA | bid | Days 1 to 14 |
| (n = 4) | 2 placebo | NA | q8h | Days 1 to 14 |
| V TF (non- | 1a | 1000 mg | bid | Days 1 to 14 |
| null) Arm 1 | 2 | 600 mg | bid | Days 1 to 14 |
| (n = 8) |  |  |  |  |
| V TF (non- | 1a placebo | NA | bid | Days 1 to 14 |
| null) Arm 2 | 2 placebo | NA | bid | Days 1 to 14 |
| (n = 2) |  |  |  |  |
| VI TF (null) | 1a | 1000 mg | bid | Days 1 to 14 |
| Arm 1 | 2 | 900 mg | bid | Days 1 to 14 |
| (n = 8) |  |  |  |  |
| VI TF (null) | 1a placebo | NA | bid | Days 1 to 14 |
| Arm 2 | 2 placebo | NA | bid | Days 1 to 14 |
| (n = 2) |  |  |  |  |
| VII Naive | 1a | 1000 mg | bid | Days 1 to 14 |
| Arm 1 | 2 | 900 mg | bid | Days 1 to 14 |
| (n = 8) |  |  |  |  |

TABLE 1-continued

| Group | Compound | Amount | Frequency | Regime |
|---|---|---|---|---|
| VII Naive Arm 2 (n = 2) | 1a placebo 2 placebo | NA NA | bid bid | Days 1 to 14 Days 1 to 14 |

* bid—twice daily
* q8h—every 8 hours
* NA—not applicable
* TF = subjects who failed the current standard of care (null, partial responders and relapsers)

Pharmacokinetic Assessments

Four mL blood samples were collected as follows:
Group I
  Compound 1a
    Day 1 predose prior to first dose of study drugs and just prior to dosing of Compound 1a at 12 hours
    Day 3 at predose and 0.5, 1, 2, 3, 4, 8 and 12 hours postdose
    Day 4 pre-morning dose
    Day 7 at predose and 0.5, 1, 2, 3, 4, 8 and 12 hours postdose
  Compound 2
    Day 1 predose prior to first dose of study drugs and just prior to dosing of Compound 2 at 8 hours
    Day 3 at predose and 0.5, 1, 1.5, 2, 3, 4 and 8 hours postdose
    Day 4 pre-morning dose
    Day 7 at predose and 0.5, 1, 1.5, 2, 3, 4 and 8 hours postdose
Groups II, III and IV
  Compound 1a
    Day 1 predose prior to first dose of study drugs and just prior to dosing of Compound 1a at 12 hours
    Day 4 pre-morning dose
    Day 7 at predose and 0.5, 1, 2, 3, 4, 8 and 12 hours postdose
    Day 14 at predose
  Compound 2
    Day 1 predose prior to first dose of study drugs and just prior to dosing of Compound 2 at 8 hours
    Day 4 pre-morning dose
    Day 7 at predose and 0.5, 1, 1.5, 2, 3, 4 and 8 hours postdose
    Day 14 at predose
Groups V, VI and VII
  Compound 1a
    Day 1 predose prior to first dose of study drugs and just prior to dosing of Compound 1a at 12 hours
    Day 4 pre-morning dose
    Day 7 at predose and 0.5, 1, 2, 3, 4, 8 and 12 hours postdose
    Day 10 at predose
    Day 14 at predose
  Compound 2
    Day 1 predose prior to first dose of study drugs and just prior to dosing of Compound 1a at 12 hours
    Day 4 pre-morning dose
    Day 7 at predose and 0.5, 1, 2, 3, 4, 8 and 12 hours postdose
    Day 10 at predose
    Day 14 at predose
  Plasma concentrations of Compound 1 (and, if applicable, its metabolites) and Compound 2 were measured by validated liquid chromatography/tandem mass spectrometry (LC-MS/MS) methods. The pharmacokinetic parameters for each compound were estimated using standard non-compartmental methods using WinNonlin (Version 5.2, Pharsight Co.) using standard methods.

HCV RNA Viral Load Determination and Viral Resistance Assessment

Blood samples for HCV RNA assessments (anti-viral activity±resistance) were collected throughout the treatment and follow-up period as follows:

Group I
  Screening
    Day 1 within 1 hour prior to morning doses and at 4 and 12 hours after morning doses
    Days 5, 6, and 7 within 1 hour prior to morning doses
    Days 8, 14, 35 and 91
Groups II, III and IV
  Screening
    Day 1 within 1 hour prior to morning doses and at 4 and 12 hours after morning doses
    Days 2, 3, and 4 within 1 hour prior to morning doses and 12 hours after morning doses
    Days 5, 6, 7, 10, 13 and 14 within 1 hour prior to morning doses
    Days 15, 21, 42 and 98
Groups V, VI and VII
  Screening
    Day 1 within 1 hour prior to morning doses and at 4, 12 and 16 hours after morning doses
    Days 2 and 14 within 1 hour prior to morning doses and 12 hours after morning doses
    Days 3 and 4 within 1 hour prior to morning doses and at 12 and 16 hours after morning doses
    Days 5, 6, 7, 10, and 13 within 1 hour prior to morning doses
    Days 21, 42 and 98

Predose samples were taken within 1 hour of dosing. Approximately 10 mL of blood was used for both the HCV RNA viral load determination and the viral resistance assessment. The HCV RNA levels were determined by COBAS® AmpilPrep/COBAS® Taqman® HCV Test RUO. This is a real-time PCR method. HCV and RNA measurements were taken at designated time points. Mean and individual plots of viral load data (absolute and change from baseline) were provided from each arm in each group. A listing of individual change from baseline was determined. Summaries of HCV RNA measurements at each nominal time point are provided by treatment arm.

Selected blood samples collected for viral load determinations were utilized for phenotypic and sequence analyses to monitor for development of resistance to Compound 1 and Compound 2 in subjects, who experience either viral load rebound or non-response while on treatment with Compound 1 and/or Compound 2.

Population sequencing of the complete coding sequence of the HCV NS5B polymerase and/or NS3/4A of all baseline samples was performed using standard sequencing technology. For subjects experiencing viral load rebound, attempts were made to determine the population NS5B coding sequence at (a) baseline and (b) at the first sample after viral load rebound. Amino acid substitutions in the samples after viral load rebound were determined as compared to the respective baseline sequence for each selected subject. Secondary analyses included sequencing the entire HCV genome, sequencing of samples derived from subjects having a virological response, and determining sequences of minority quasispecies. Phenotype studies to monitor for resistance to Compound 1 and to Compound 2 of the samples outlined in (a) and (b) were performed, and included analysis of samples derived from subjects having a virological response. Assessment of cross resistance to other HCV inhibitors and sequences analyses were performed on selected samples and may require amplification and subcloning of sequences from the HCV genome.

Table 2 provides the viral kinetic results for Group I, Arms 1 and 2, and monotherapy treatment with Compound 1a or Compound 2 after 7 days of treatment. The results show the mean log change from baseline of HCV RNA polymerase (IU/mL).

TABLE 2

| | |
|---|---|
| Arm 1 | −2.9 |
| Arm 2 | −3.2 |
| Compound 2 monotherapy 100 mg, q8h | −1.7 |
| Compound 1a monotherapy 750 mg, bid | −1.3 |

As shown from the results in Table 2, subjects treated with the combination of Compounds 1a and 2 showed a decrease in viral load compared to subjects treated with Compound 1a or Compound 2 as monotherapy.

Tables 3 and 4 provide the virological results for Groups I-VII. Subjects treated with the combination of Compounds 1a and 2, without pegylated interferon or ribavin, experienced a median reduction in viral levels of −4.8 to −4.6 $\log_{10}$ IU/mL in all regimens and patient populations tested. Furthermore, patient's viral load became undetectable when switched to the standard of care.

Determination of Serum ALT

Figure 4:
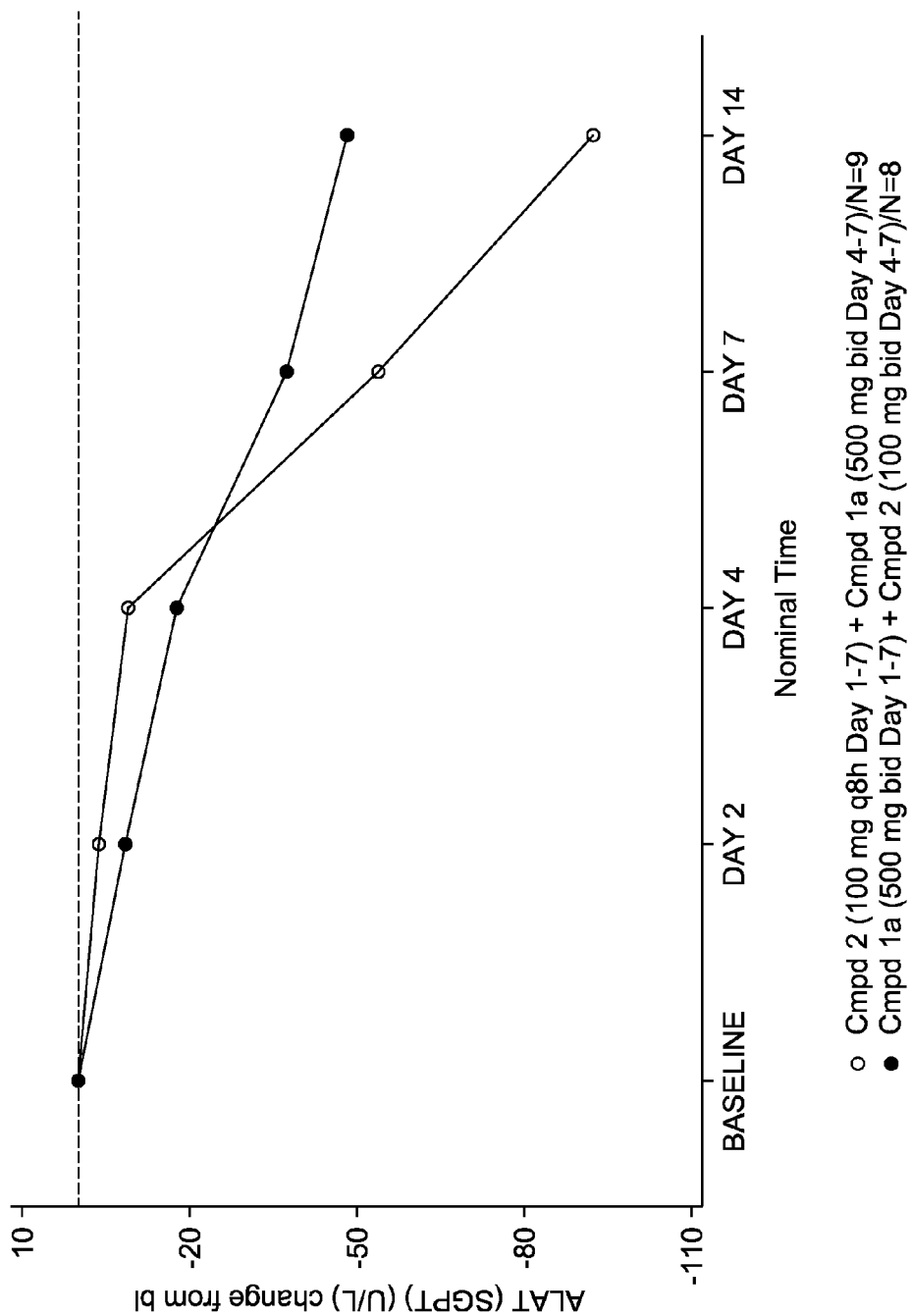
FIG. 4 is a graph showing the changes in the level of serum alanine aminotransferase (ALT) over 14 days of treatment with Compound 1a and Compound 2.

Serum ALT activity was measured using a standard routine blood work test(s). The baseline value was obtained prior to the first dose. Values outside the normal ranges and marked abnormalities were flagged according to the standard definitions of Roche. The values and changes from baseline were plotted by individual subjects to aid with data evaluation. A transformation of the data was performed. The mean change from baseline of serum ALT for Group II is shown in FIG. 4. As shown in FIG. 4, the combination of Compounds 1a and 2 reduces serum ALT activity.

Safety and Tolerability

Provided in Table 5 are the safety and tolerability results for the combination treatment using Compounds 1a and 2, with and without pegylated interferon and/or ribavirin. As shown by the results in Table 5, the combination treatment of Compounds 1a and 2 is safe and well tolerated.

TABLE 3

| Regimen 1a mg/2 mg | Group | n | Patient Population | NCV RNA change from baseline ($\text{Log}_{10}$ IU/mL) median (range) | HCV RNA < LLOQ (<43 IU/mL) N (%) | HCV RNA < LLOD (<15 IU/mL) N (%) |
|---|---|---|---|---|---|---|
| 500/100 | II | 8 | Naive | −3.9 (−5.0 to −2.9) | 1/8 (13) | 1/8 (13) |
| 500/200 | III | 8 | Naive | −5.2 (−5.5 to −3.1) | 5/8 (63) | 2/8 (25) |
| 1000/100 | III | 7 | Naive | −4.8 (−5.7 to −4.5) | 5/7 (71) | 2/7 (29) |
| 1000/200 | IV | 8 | Naive | −4.8 (−5.5 to −2.7) | 5/8 (63) | 2/8 (25) |

LLOQ = lower limit of quantification by Roche TaqMan Assay (<43 IU/mL)

LLOD = lower limit of detection by Roche TaqMan Assay (<15 IU/mL)

TABLE 4

| Regimen 1a mg/2 mg | Group | n | Patient Population | NCV RNA change from baseline ($\text{Log}_{10}$ IU/mL) median (range) | HCV RNA < LLOQ (<43 IU/mL) N (%) | HCV RNA < LLOD (<15 IU/mL) N (%) |
|---|---|---|---|---|---|---|
| 1000/600 | V | 8 | TF non-null | −4.0 (−6.0 to −2.5) | 4/8 (50) | 1/8 (13) |
| 1000/900 | VI | 8 | TF-null | −4.9 (−5.3 to −3.5) | 4/8 (50) | 2/8 (25) |
| 1000/900 | VII | 8 | Naive | −5.1 (−5.9 to −3.0) | 7/8 (88) | 5/8 (63) |

LLOQ = lower limit of quantification by Roche TaqMan Assay (<43 IU/mL)

LLOD = lower limit of detection by Roche TaqMan Assay (<15 IU/mL)

TABLE 5

| | Group | | | | | | |
|---|---|---|---|---|---|---|---|
| | Group I | Group II | Group III | Group IV | Group V | Group VI | Group VII* |
| Serious Adverse Events | 0 | 0 | 0 | 0 | 0 | 0 | 0 |
| Discontinuations | 0 | 0 | 0 | 0 | 0 | 0 | 0 |
| Grade 3/4 Laboratory Abnormalities | 0 | 0 | 0 | 0 | 0 | 0 | 0 |
| Total Adverse Events | 16/17 | 15/12 | 18/18 | 14/12 | 13/10 | 12/10 | 4/10 |
| Headache | 6 | 1 | 5 | 5 | 5 | 4 | 1 |
| Disturbance in Attention | 0 | 0 | 0 | 1 | 1 | 0 | 0 |
| Dysgeusia | 0 | 0 | 1 | 0 | 1 | 0 | 0 |
| Nausea | 1 | 1 | 0 | 0 | 0 | 4 | 0 |
| Diarrhea | 1 | 1 | 1 | 0 | 0 | 2 | 0 |
| Dry Mouth | 0 | 2 | 0 | 1 | 0 | 0 | 0 |
| Abdominal pain/Discomfort | 1 | 0 | 1 | 1 | 2 | 0 | 0 |
| Dyspepsia | 0 | 0 | 1 | 1 | 0 | 0 | 0 |
| Rash | 2 | 0 | 0 | 0 | 1 | 0 | 0 |
| Dry Eyes | 0 | 1 | 2 | 0 | 0 | 0 | 0 |
| Fatigue | 1 | 0 | 1 | 0 | 0 | 0 | 0 |
| Chest Pain | 0 | 1 | 0 | 0 | 0 | 0 | 1 |
| Palpitations | 1 | 0 | 1 | 0 | 1 | 0 | 0 |
| Uncoded Adverse Events | 0 | 1 | 0 | 2 | 1 | 0 | 2 |

*Group VII - one subject in treatment

It will be understood by those of skill in the art that numerous and various modifications can be made without departing from the spirit of the present application. Therefore, it should be clearly understood that the forms of the present application are illustrative only and not intended to limit the scope of the present application.

What is claimed is:

1. A composition comprising a first compound, or a pharmaceutically acceptable salt thereof, wherein the first compound is

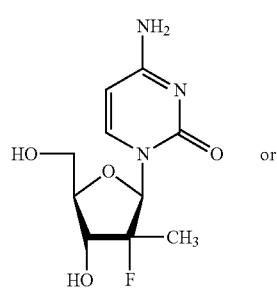

or

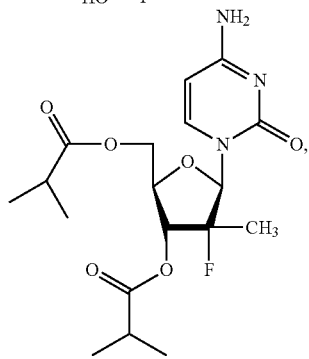

and a second compound, or a pharmaceutically acceptable salt thereof, wherein the second compound is

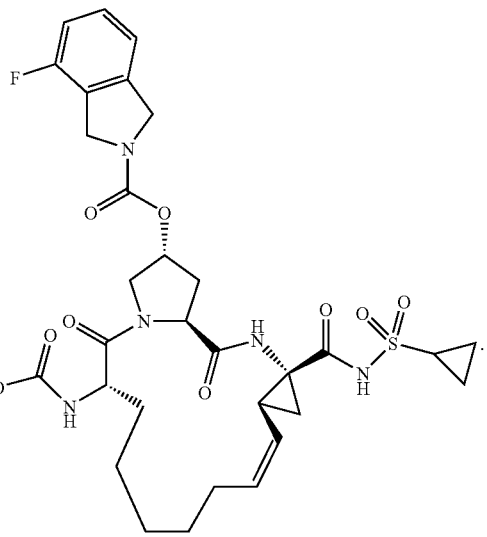

2. A composition consisting essentially of a first compound, or a pharmaceutically acceptable salt thereof, wherein the first compound is

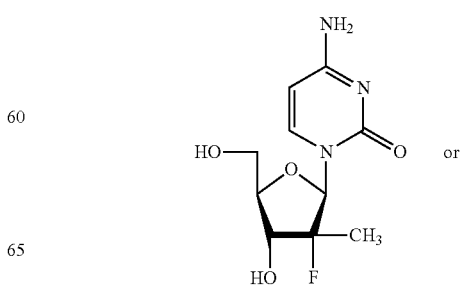

or

-continued

[chemical structure]

and a second compound, or a pharmaceutically acceptable salt thereof, wherein the second compound is

[chemical structure]

3. The composition of claim 1, further comprising a pharmaceutically acceptable excipient, diluent or carrier.

4. The composition of claim 1, wherein the composition comprises an amount of the first compound, or a pharmaceutically acceptable salt thereof, in the range of about 9000 mg to about 50 mg.

5. The composition of claim 1, wherein the composition comprises an amount of the first compound, or a pharmaceutically acceptable salt thereof, in the range of about 5000 mg to about 150 mg.

6. The composition of claim 1, wherein the composition comprises an amount of the first compound, or a pharmaceutically acceptable salt thereof, in the range of about 2000 mg to about 300 mg.

7. The composition of claim 1, wherein the composition comprises an amount of the first compound, or a pharmaceutically acceptable salt thereof, in the range of about 1000 mg to about 450 mg.

8. The composition of claim 1, wherein the composition comprises an amount of the first compound, or a pharmaceutically acceptable salt thereof, in the range of about 1000 mg to about 500 mg.

9. The composition of claim 1, wherein the composition comprises an amount of the second compound, or a pharmaceutically acceptable salt thereof, in the range of about 2000 mg to about 2 mg.

10. The composition of claim 1, wherein the composition comprises an amount of the second compound, or a pharmaceutically acceptable salt thereof, in the range of about 1600 mg to about 25 mg.

11. The composition of claim 1, wherein the composition comprises an amount of the second compound, or a pharmaceutically acceptable salt thereof, in the range of about 500 mg to about 50 mg.

12. The composition of claim 1, wherein the composition comprises an amount of the second compound, or a pharmaceutically acceptable salt thereof, in the range of about 200 mg to about 100 mg.

13. The composition of claim 1, wherein the composition comprises a total amount of the first compound, or a pharmaceutically acceptable salt thereof, in the range of about 1% to about 99% (weight/weight) based on the sum of the total amount of the first compound, or a pharmaceutically acceptable salt thereof, and the total amount of the second compound, or a pharmaceutically acceptable salt thereof, in the composition.

14. The composition of claim 1, wherein the composition comprises a total amount of the first compound, or a pharmaceutically acceptable salt thereof, in the range of about 5% to about 90% (weight/weight) based on the sum of the total amount of the first compound, or a pharmaceutically acceptable salt thereof, and the total amount of the second compound, or a pharmaceutically acceptable salt thereof, in the composition.

15. The composition of claim 1, wherein the composition comprises a total amount of the first compound, or a pharmaceutically acceptable salt thereof, in the range of about 10% to about 80% (weight/weight) based on the sum of the total amount of the first compound, or a pharmaceutically acceptable salt thereof, and the total amount of the second compound, or a pharmaceutically acceptable salt thereof, in the composition.

16. The composition of claim 1, wherein the composition comprises a total amount of the first compound, or a pharmaceutically acceptable salt thereof, in the range of about 20% to about 70% (weight/weight) based on the sum of the total amount of the first compound, or a pharmaceutically acceptable salt thereof, and the total amount of the second compound, or a pharmaceutically acceptable salt thereof, in the composition.

17. The composition of claim 1, wherein the composition comprises a total amount of the first compound, or a pharmaceutically acceptable salt thereof, in the range of about 30% to about 60% (weight/weight) based on the sum of the total amount of the first compound, or a pharmaceutically acceptable salt thereof, and the total amount of the second compound, or a pharmaceutically acceptable salt thereof, in the composition.

18. The composition of claim 1, wherein the composition comprises a total amount of the first compound, or a pharmaceutically acceptable salt thereof, in the range of about 40% to about 50% (weight/weight) based on the sum of the total amount of the first compound, or a pharmaceutically acceptable salt thereof, and the total amount of the second compound, or a pharmaceutically acceptable salt thereof, in the composition.

19. The composition of claim 13, wherein the composition comprises a total amount of the second compound, or a pharmaceutically acceptable salt thereof, in the range of about 1% to about 99% (weight/weight) based on the sum of the total amount of the first compound, or a pharmaceutically acceptable salt thereof, and the total amount of the second compound, or a pharmaceutically acceptable salt thereof, in the composition.

20. The composition of claim 13, wherein the composition comprises a total amount of the second compound, or a pharmaceutically acceptable salt thereof, in the range of about 5% to about 90% (weight/weight) based on the sum of the total amount of the first compound, or a pharmaceutically acceptable salt thereof, and the total amount of the second compound, or a pharmaceutically acceptable salt thereof, in the composition.

21. The composition of claim 13, wherein the composition comprises a total amount of the second compound, or a pharmaceutically acceptable salt thereof, in the range of about 10% to about 80% (weight/weight) based on the sum of the total amount of the first compound, or a pharmaceutically acceptable salt thereof, and the total amount of the second compound, or a pharmaceutically acceptable salt thereof, in the composition.

22. The composition of claim 13, wherein the composition comprises a total amount of the second compound, or a pharmaceutically acceptable salt thereof, in the range of about 20% to about 70% (weight/weight) based on the sum of the total amount of the first compound, or a pharmaceutically acceptable salt thereof, and the total amount of the second compound, or a pharmaceutically acceptable salt thereof, in the composition.

23. The composition of claim 13, wherein the composition comprises a total amount of the second compound, or a pharmaceutically acceptable salt thereof, in the range of about 30% to about 60% (weight/weight) based on the sum of the total amount of the first compound, or a pharmaceutically acceptable salt thereof, and the total amount of the second compound, or a pharmaceutically acceptable salt thereof, in the composition.

24. The composition of claim 13, wherein the composition comprises a total amount of the second compound, or a pharmaceutically acceptable salt thereof, in the range of about 40% to about 50% (weight/weight) based on the sum of the total amount of the first compound, or a pharmaceutically acceptable salt thereof, and the total amount of the second compound, or a pharmaceutically acceptable salt thereof, in the composition.

25. The composition of claim 1, wherein the amount of the first compound, or a pharmaceutically acceptable salt thereof, in the composition is less than the amount of the first compound, or a pharmaceutically acceptable salt thereof, needed to achieve substantially the same viral load reduction as when the first compound, or a pharmaceutically acceptable salt thereof, is administered as monotherapy.

26. The composition of claim 1, wherein the amount of the second compound, or a pharmaceutically acceptable salt thereof, in the composition is less than the amount of the second compound, or a pharmaceutically acceptable salt thereof, needed to achieve substantially the same viral load reduction as when the second compound, or a pharmaceutically acceptable salt thereof, is administered as monotherapy.

27. The composition of claim 1, wherein the composition further comprises one or more additional therapeutic agents.

28. The composition of claim 27, wherein the one or more additional therapeutic agents are selected from the group consisting of a nucleoside analog, pirfenidone, a pirfenidone analog, an NS5B RNA-dependent RNA polymerase inhibitor, a tumor necrosis factor antagonist, thymosin-α, interferon-gamma (IFN-γ), interferon-alpha (IFN-α), 3'-azidothymidine, 2',3'-dideoxyinosine, 2',3'-dideoxycytidine, 2-,3-didehydro-2',3'-dideoxythymidine, combivir, abacavir, adefovir dipivoxil, cidofovir, ritonavir, an inosine monophosphate dehydrogenase inhibitor, an interferon, an additional NS3 protease inhibitor, a NS5B polymerase inhibitor, and an NS3 helicase inhibitor.

29. The composition of claim 28, wherein the nucleoside analog is selected from the group consisting of ribavirin, levovirin, viramidine, an L-nucleoside, and isatoribine.

30. The composition of claim 28, wherein the tumor necrosis factor antagonist is selected from the group consisting of etanercept, infliximab, and adalimumab.

31. The composition of claim 28, wherein the thymosin-α is in an amount in the range of from about 1.0 mg to about 1.6 mg.

32. The composition of claim 28, wherein the IFN-γ is in an amount in the range of from about 10 μg to about 300 μg.

33. The composition of claim 28, wherein the IFN-α is monoPEG (30 kD, linear)-ylate consensus.

34. The composition of claim 28, wherein the IFN-α is selected from the group consisting of a 40 kD branched mono-methoxy PEG conjugate of interferon α-2b and a 12 kD mono-methoxy PEG conjugate of interferon α-2b.

35. The composition of claim 28, wherein the IFN-α is INFERGEN consensus IFN-α.

36. The composition of claim 28, wherein the additional NS3 protease inhibitor is selected from

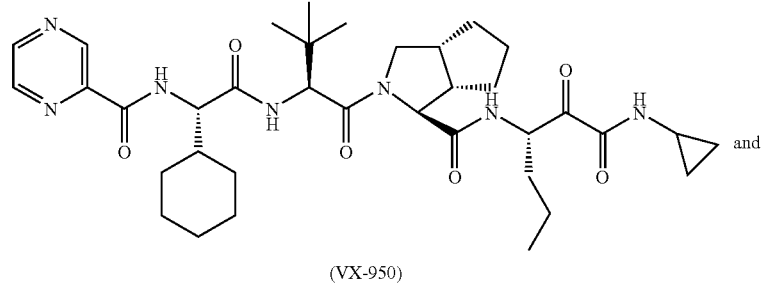

(VX-950)

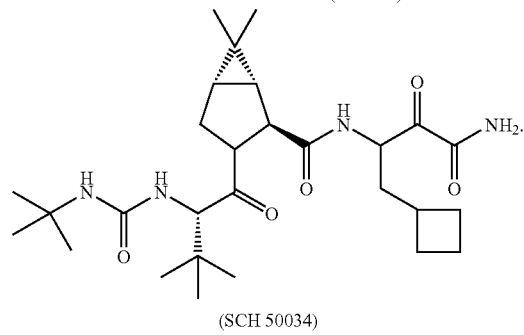

(SCH 50034)

37. The composition of claim 1, wherein the composition does not comprise ribavirin.

38. The composition of claim 1, wherein the composition does not comprise an interferon.

39. The composition of claim 38, wherein the interferon is a pegylated interferon.

40. A method for ameliorating a disease condition in a patient population, comprising administering a therapeutically effective amount of one or more compositions of claim 1 to a subject suffering from the disease condition, wherein the disease condition is selected from the group consisting of a hepatitis C virus infection, and liver fibrosis.

41. A method for ameliorating a disease condition in a patient population comprising administering a therapeutically effective amount of a first compound, or a pharmaceutically acceptable salt thereof, wherein the first compound is

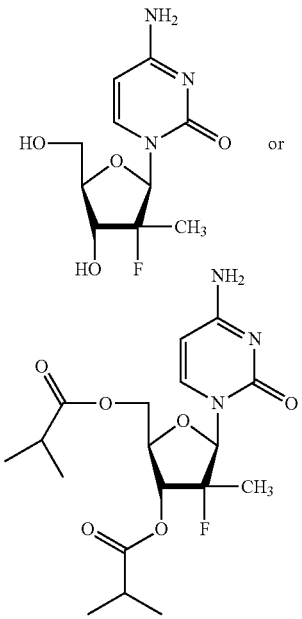

and a therapeutically effective amount of a second compound, or a pharmaceutically acceptable salt thereof, wherein the second compound is

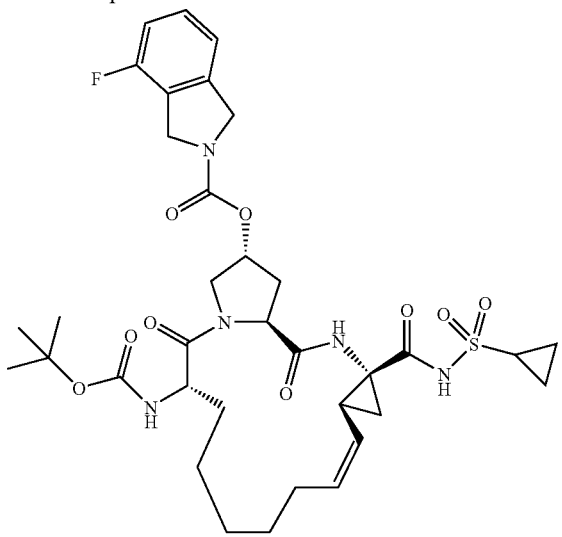

to a subject suffering from the disease condition, wherein the disease condition is selected from the group consisting of a hepatitis C virus infection, and liver fibrosis.

42. The method of claim 41, wherein the first compound, or a pharmaceutically acceptable salt thereof, is administered before the second compound, or a pharmaceutically acceptable salt thereof.

43. The method of claim 41, wherein the first compound, or a pharmaceutically acceptable salt thereof, is administered after the second compound, or a pharmaceutically acceptable salt thereof.

44. The method of claim 41, wherein the first compound, or a pharmaceutically acceptable salt thereof, is administered at approximately the same time as the second compound, or a pharmaceutically acceptable salt thereof.

45. The method of claim 41, wherein the first compound, or a pharmaceutically acceptable salt thereof, and the second compound, or a pharmaceutically acceptable salt thereof, are together in one dosage form.

46. The method of claim 41, wherein the first compound, or a pharmaceutically acceptable salt thereof, and the second compound, or a pharmaceutically acceptable salt thereof, are in separate dosage forms.

47. The method of claim 40, wherein the disease condition is a hepatitis C viral infection.

48. The method of claim 40, wherein the method further comprises administering an effective amount of an additional nucleoside analog.

49. The method of claim 48, wherein the additional nucleoside analog is selected from the group consisting of ribavirin, levovirin, viramidine, an L-nucleoside, and isatoribine.

50. The method of claim 40, wherein the method further comprises administering an effective amount of pirfenidone or a pirfenidone analog.

51. The method of claim 40, wherein the method further comprises administering an effective amount of an NS5B RNA-dependent RNA polymerase inhibitor.

52. The method of claim 40, wherein the method further comprises administering an effective amount of a tumor necrosis factor antagonist selected from the group consisting of etanercept, infliximab, and adalimumab.

53. The method of claim 40, wherein the method further comprises administering an effective amount of thymosin-α.

54. The method of claim 53, wherein the thymosin-α is in an amount in the range of from about 1.0 mg to about 1.6 mg.

55. The method of claim 40, wherein the method further comprises administering an effective amount of interferon-gamma (IFN-γ).

56. The method of claim 55, wherein the IFN-γ is administered subcutaneously in an amount in the range of from about 10 μg to about 300 μg.

57. The method of claim 40, wherein the method further comprises administering an effective amount of interferon-alpha (IFN-α).

58. The method of claim 57, wherein the IFN-α is monoPEG (30 kD, linear)-ylate consensus administered at a dosing interval in the range of every 8 days to every 14 days.

59. The method of claim 57, wherein the IFN-α is monoPEG (30 kD, linear)-ylated consensus IFN-α administered at a dosing interval of once every 7 days.

60. The method of claim 57, wherein the IFN-α is selected from the group consisting of a 40 kD branched mono-methoxy PEG conjugate of interferon α-2b and a 12 kD mono-methoxy PEG conjugate of interferon α-2b.

61. The method of claim 57, wherein the IFN-α is INFERGEN consensus IFN-α.

62. The method of claim 40, wherein the method further comprises administering an effective amount of an agent selected from 3'-azidothymidine, 2',3'-dideoxyinosine, 2',3'-dideoxycytidine, 2-,3-didehydro-2',3'-dideoxythymidine, combivir, abacavir, adefovir dipivoxil, cidofovir, ritonavir, and an inosine monophosphate dehydrogenase inhibitor.

63. The method of claim 40, wherein the method further comprises administering an effective amount of an interferon, an additional NS3 protease inhibitor, an NS5B polymerase inhibitor, or an NS3 helicase inhibitor.

64. The method of claim 63, wherein the additional NS3 protease inhibitor is selected from

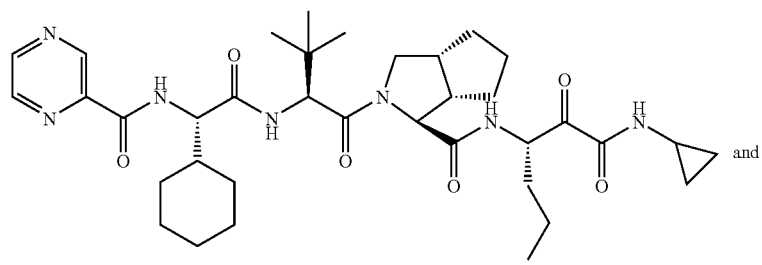

(VX-950)

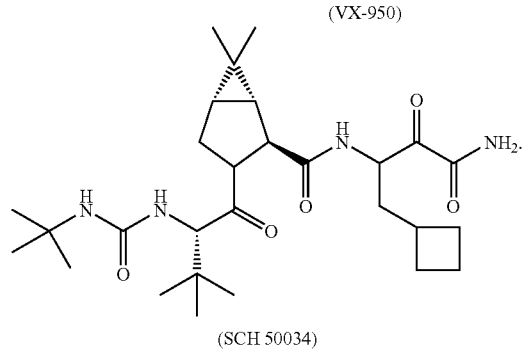

(SCH 50034)

65. The method of claim 40, wherein the patient population is administered pegylated interferon after administration of the first compound, or a pharmaceutically acceptable salt thereof, and the second compound, or a pharmaceutically acceptable salt thereof, is complete.

66. The method of claim 40, wherein the patient population is administered ribavirin after administration of the first compound, or a pharmaceutically acceptable salt thereof, and the second compound, or a pharmaceutically acceptable salt thereof, is complete.

67. The method of claim 40, wherein the method does not include administering an additional agent.

68. The method of claim 67, wherein the additional agent is ribavirin.

69. The method of claim 67, wherein the additional agent is an interferon.

70. The method of claim 69, wherein the interferon is a pegylated interferon.

* * * * *